US007736353B2

(12) United States Patent
Reynolds

(10) Patent No.: US 7,736,353 B2
(45) Date of Patent: Jun. 15, 2010

(54) PHARMACEUTICAL DELIVERY SYSTEMS AND METHODS FOR USING SAME

(75) Inventor: David L. Reynolds, Bromont (CA)

(73) Assignee: Duoject Medical Systems Inc., Bromont, Quebec (CA)

( * ) Notice: Subject to any disclaimer, the term of this patent is extended or adjusted under 35 U.S.C. 154(b) by 565 days.

(21) Appl. No.: 10/540,230

(22) PCT Filed: Jan. 22, 2004

(86) PCT No.: PCT/CA2004/000064

§ 371 (c)(1), (2), (4) Date: Jun. 21, 2005

(87) PCT Pub. No.: WO2004/064706

PCT Pub. Date: Aug. 5, 2004

(65) Prior Publication Data

US 2006/0184137 A1  Aug. 17, 2006

Related U.S. Application Data

(60) Provisional application No. 60/441,352, filed on Jan. 22, 2003, provisional application No. 60/518,345, filed on Nov. 10, 2003.

(51) Int. Cl.
*A61M 5/32* (2006.01)
(52) U.S. Cl. ...................... 604/414; 604/411
(58) Field of Classification Search ......... 604/403–416, 604/4.01–6.16, 83, 86, 87, 88, 239, 244, 604/256, 264, 272
See application file for complete search history.

(56) References Cited

U.S. PATENT DOCUMENTS

| 3,490,437 A | | 1/1970 | Bakondy et al. |
| 3,563,373 A | | 2/1971 | Paulson |
| 4,180,070 A | * | 12/1979 | Genese ........................ 604/88 |
| 4,191,225 A | | 3/1980 | Ogle |
| 4,259,956 A | | 4/1981 | Ogle |

(Continued)

FOREIGN PATENT DOCUMENTS

CH  676548  2/1991

(Continued)

*Primary Examiner*—Leslie R Deak
*Assistant Examiner*—Philip R Wiest
(74) *Attorney, Agent, or Firm*—Eric Fincham

(57) ABSTRACT

An assembly for transferring a fluid between a vessel having a body with an open end and a slidable piston positioned within the body and a vial having a penetrable seal. The assembly includes a housing having first and second open ends, and a bore extending between the first and second open ends. The housing is removably connectable to the piston. The assembly also includes a conduit having first and second ends and first and second apertures adjacent to the first and second ends, respectively. The present invention provides for an assembly for transferring a fluid between a vessel having a body with an open end and a slidable piston positioned within the body and a vial having a penetrable seal. The assembly includes a housing having first and second open ends, and a bore extending between the first and second open ends. The housing is removably connectable to the piston. The assembly also includes a conduit having first and second ends and first and second apertures adjacent to the first and second ends, respectively.

40 Claims, 29 Drawing Sheets

U.S. PATENT DOCUMENTS

| | | |
|---|---|---|
| 4,861,335 A | 8/1989 | Reynolds |
| 4,874,381 A | 10/1989 | Vetter |
| 5,069,670 A | 12/1991 | Vetter et al. |
| 5,080,649 A | 1/1992 | Vetter |
| RE34,845 E | 1/1995 | Vetter et al. |
| 5,393,497 A * | 2/1995 | Haber et al. ................. 422/103 |
| 5,527,306 A * | 6/1996 | Haining ...................... 604/411 |
| 5,569,191 A | 10/1996 | Meyer |
| 5,603,695 A | 2/1997 | Erickson |
| 5,607,399 A | 3/1997 | Grimard et al. |
| 5,667,495 A | 9/1997 | Bitdinger et al. |
| 5,700,247 A | 12/1997 | Grimard et al. |
| 5,709,666 A | 1/1998 | Reynolds |
| 5,791,466 A | 8/1998 | Tsals |
| 5,795,337 A | 8/1998 | Grimard |
| 5,803,918 A | 9/1998 | Vetter et al. |
| 5,833,659 A | 11/1998 | Kranys |
| 6,149,623 A | 11/2000 | Reynolds |
| 6,253,804 B1 * | 7/2001 | Safabash ..................... 141/97 |
| 6,296,625 B1 | 10/2001 | Vetter et al. |
| 6,582,415 B1 * | 6/2003 | Fowles et al. ............... 604/413 |
| 6,746,438 B1 * | 6/2004 | Arnissolle ................... 604/411 |
| 2004/0260248 A1 * | 12/2004 | Koller et al. ................ 604/220 |

FOREIGN PATENT DOCUMENTS

| | | |
|---|---|---|
| GB | 1372549 | 10/1974 |
| WO | WO 93/09825 | 5/1993 |
| WO | WO 95/32015 | 11/1995 |
| WO | WO 00/13723 | 3/2000 |
| WO | WO 00/54723 | 9/2000 |
| WO | WO 2004/064706 | 8/2004 |

* cited by examiner

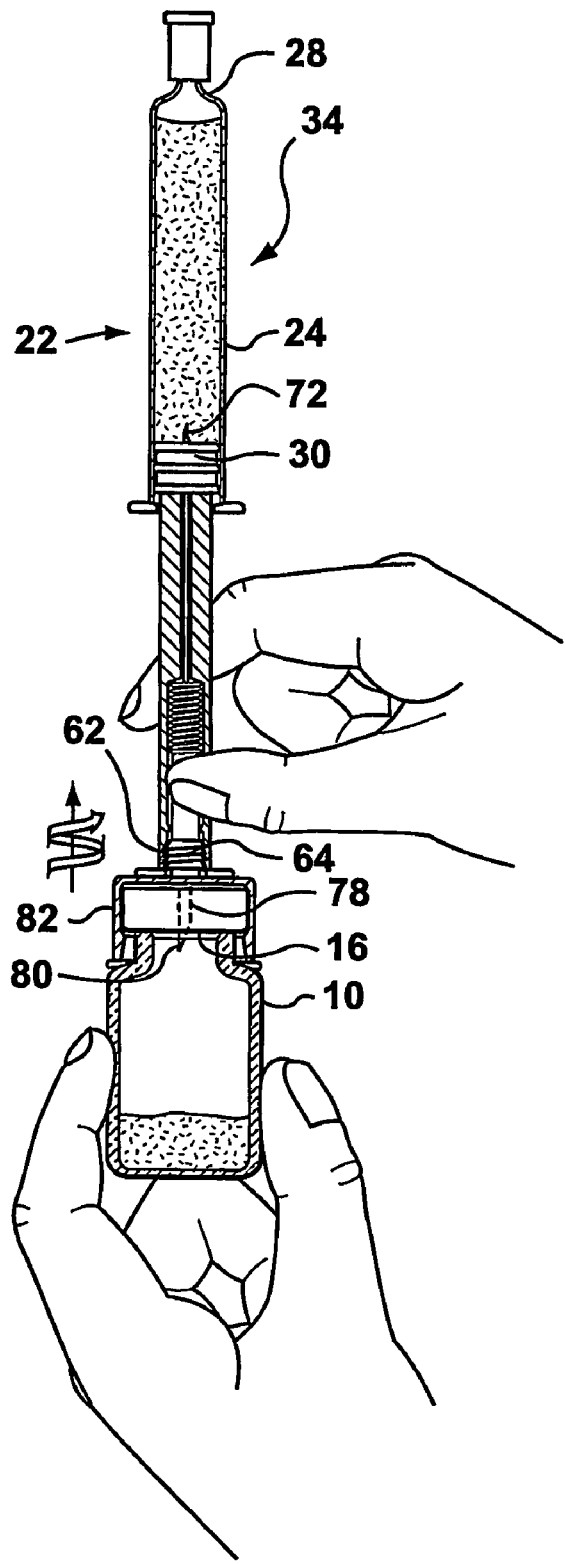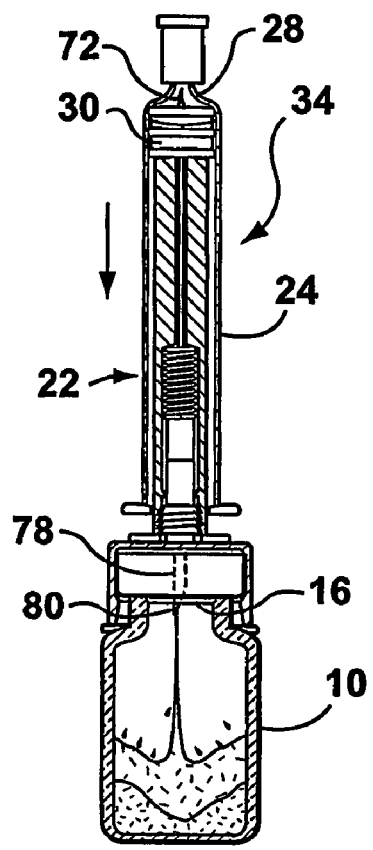
FIG. 4
FIG. 5

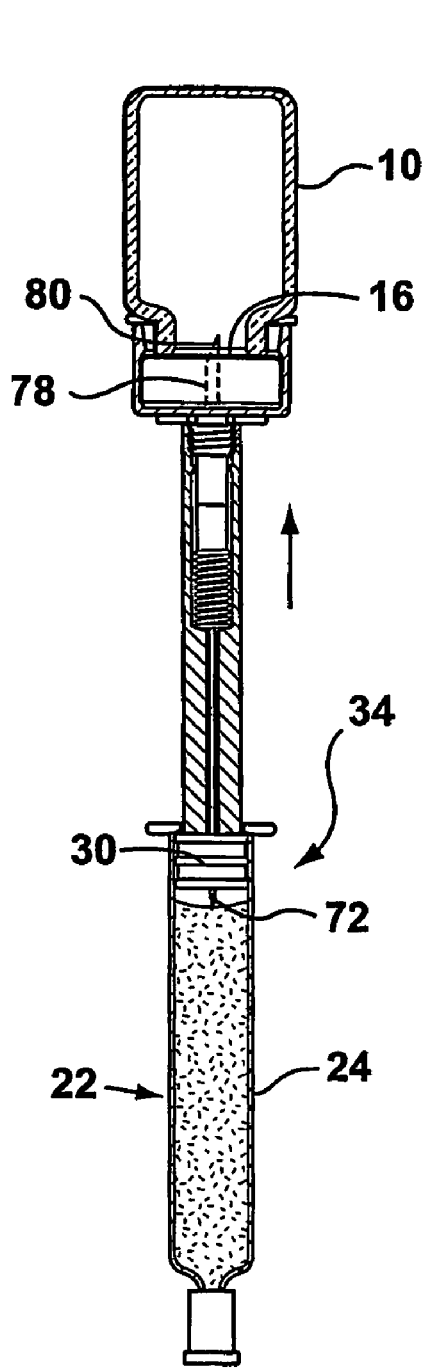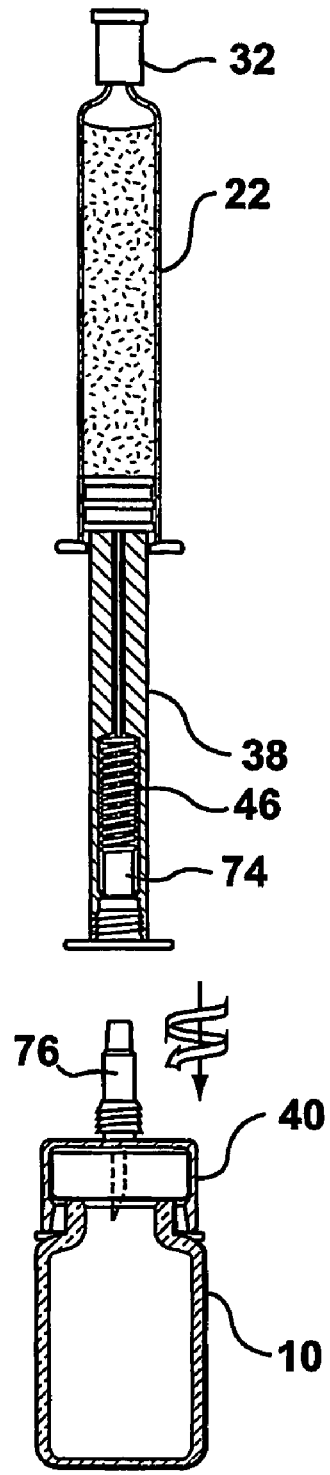
FIG. 12
FIG. 13

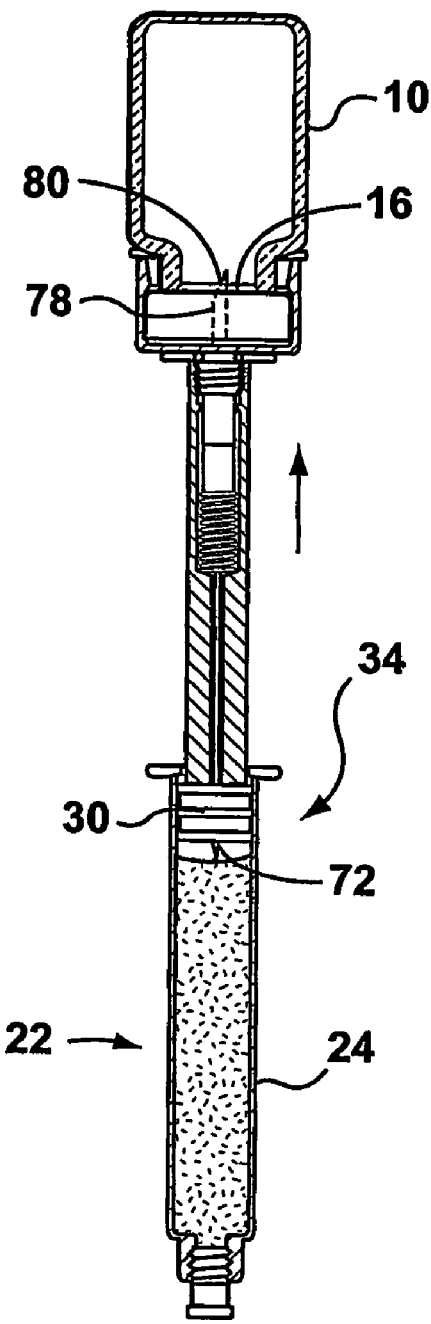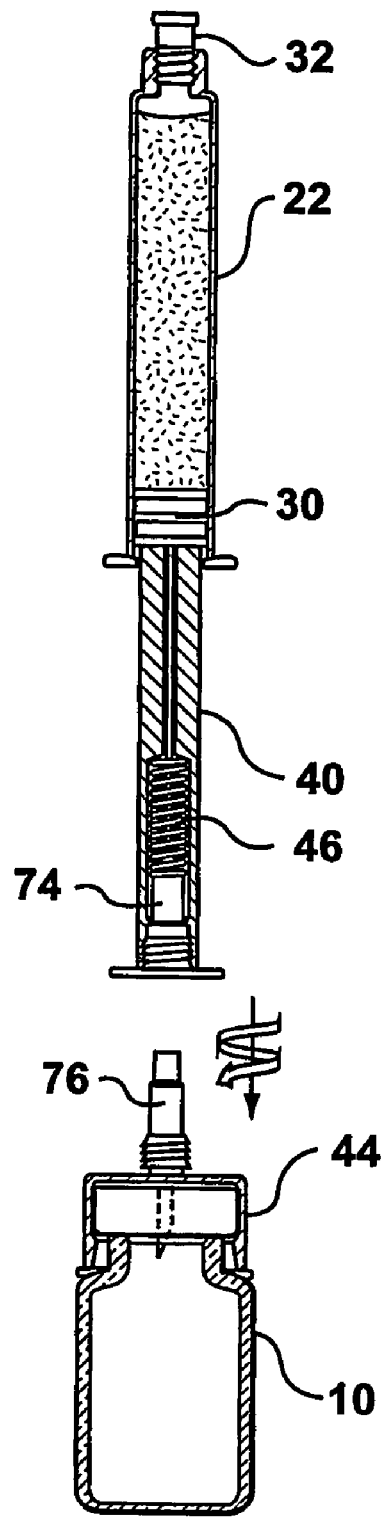
FIG. 18
FIG. 19

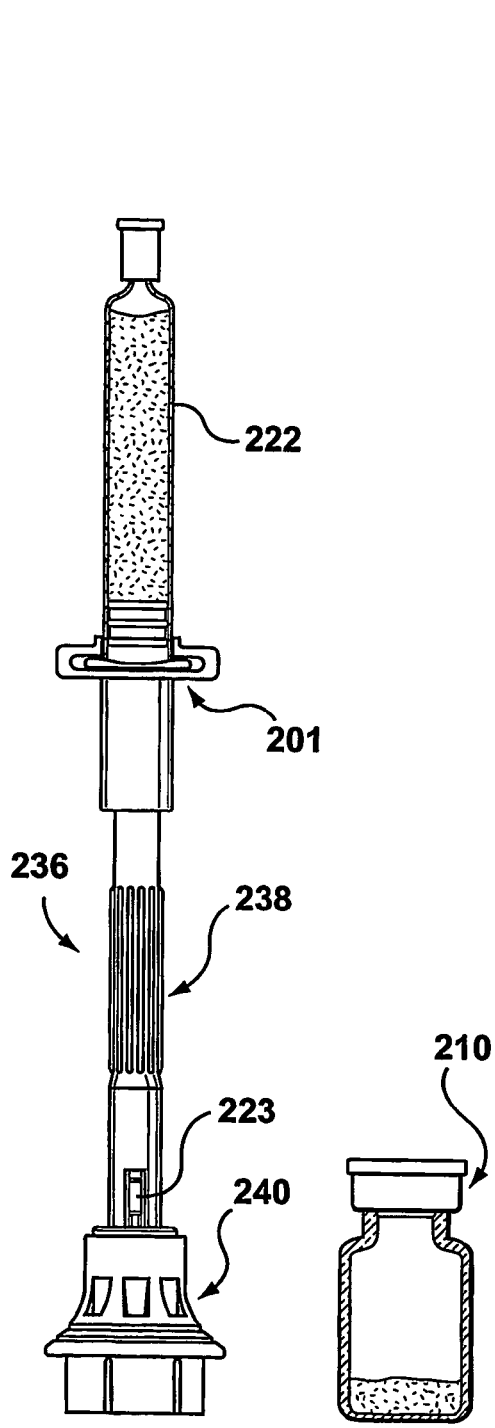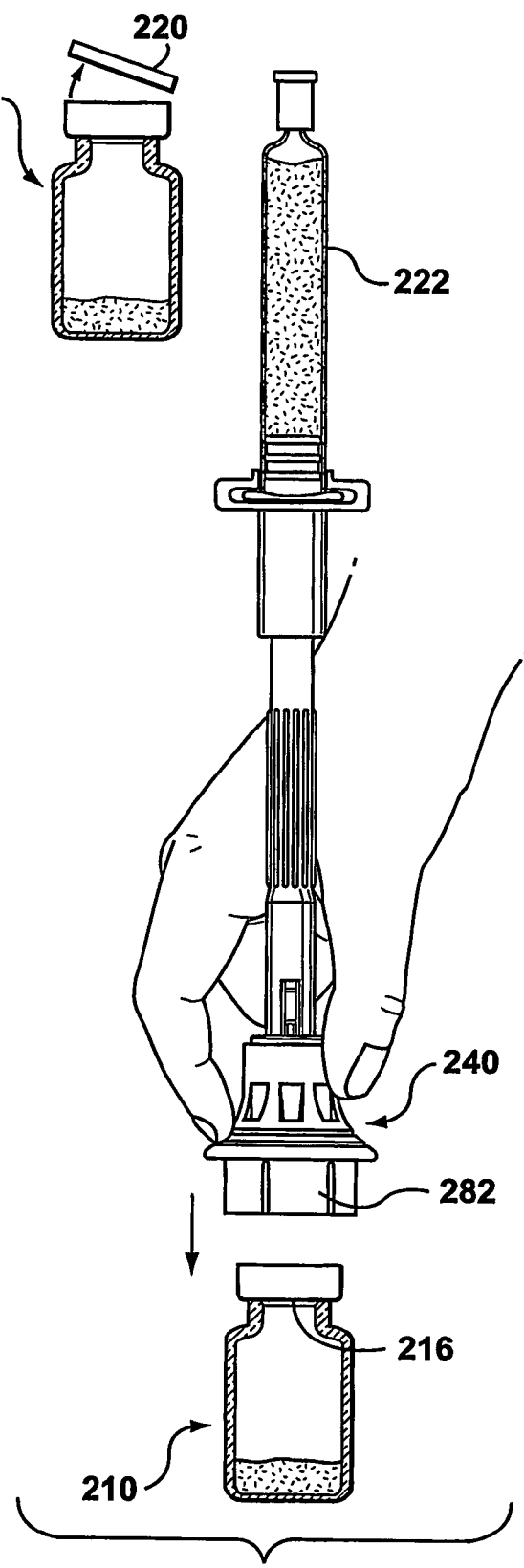
FIG. 32
FIG. 33

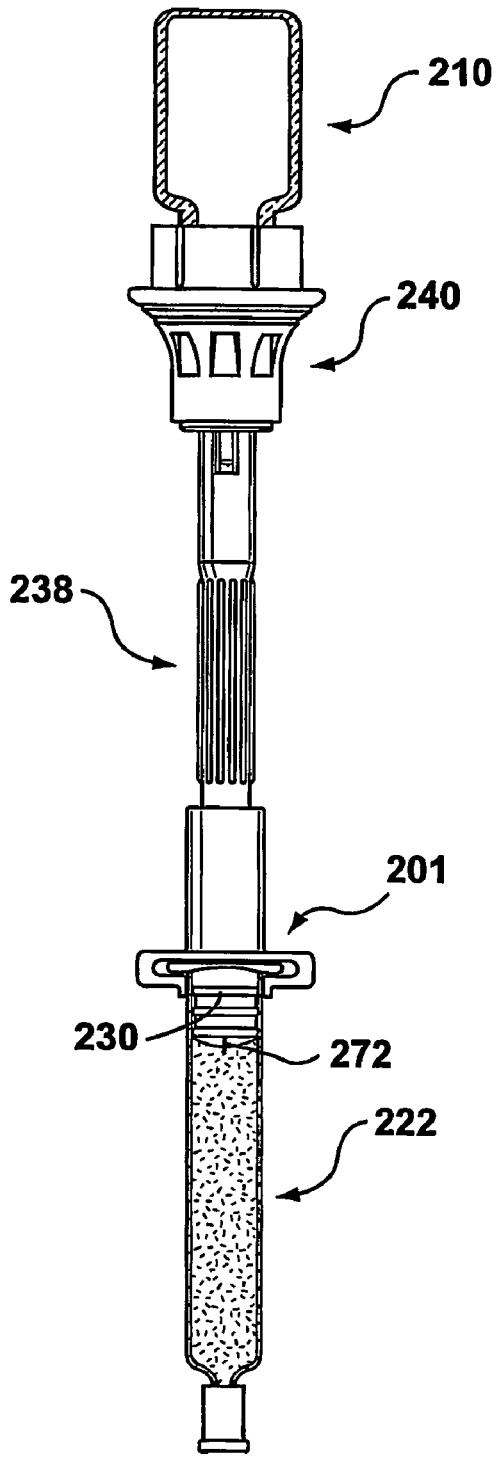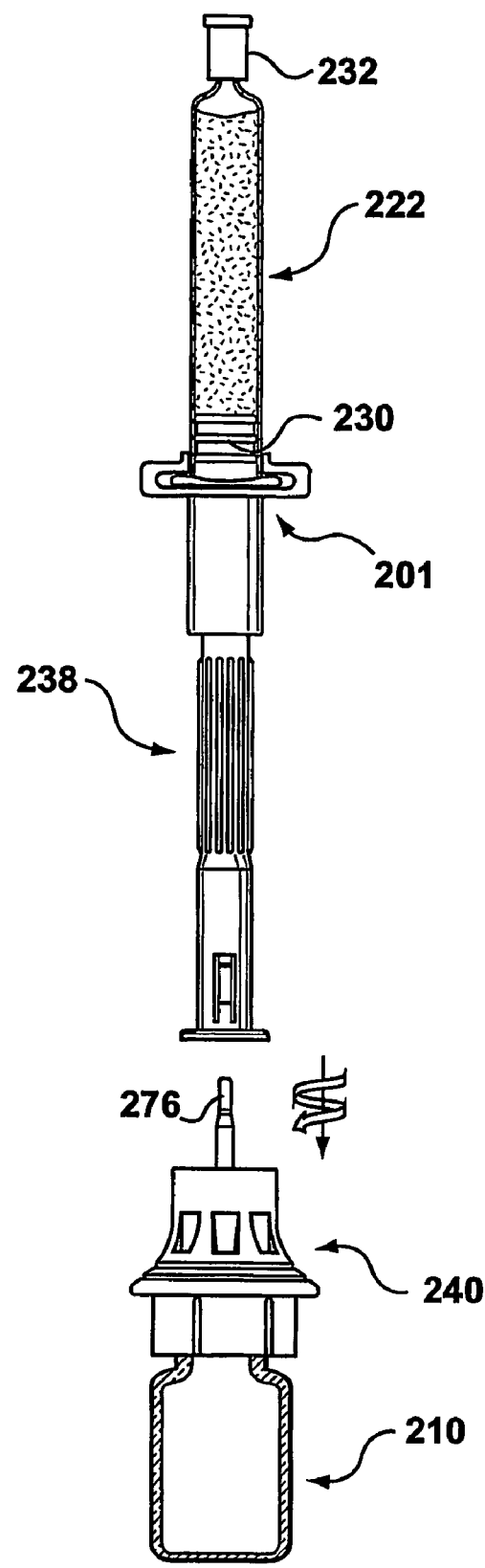
FIG. 36
FIG. 37

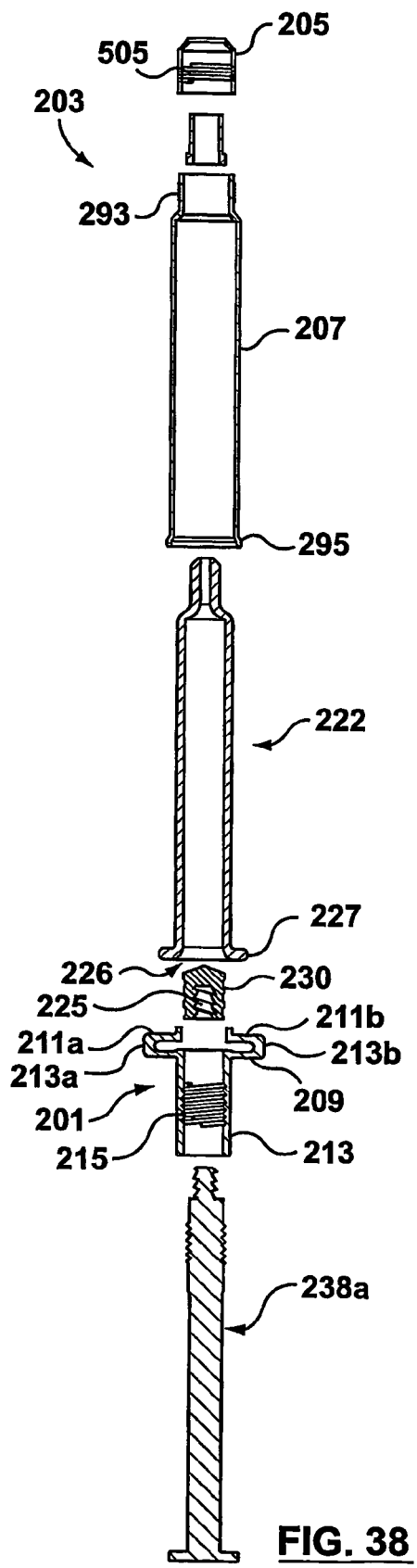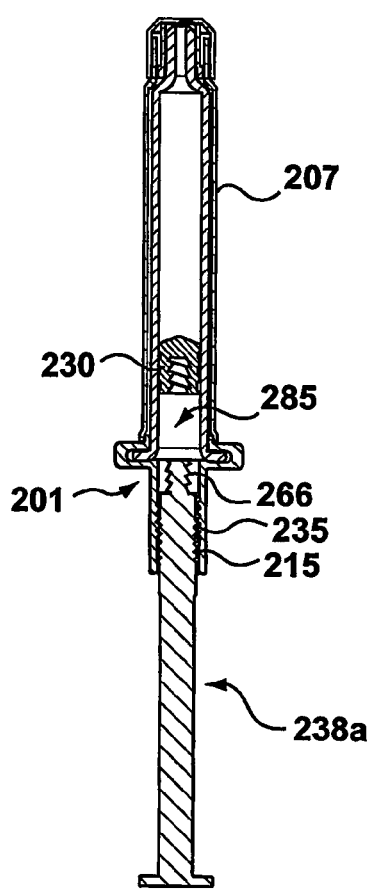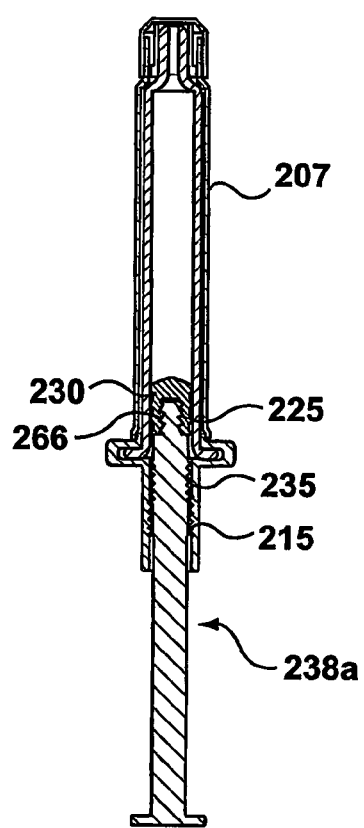
FIG. 38
FIG. 39
FIG. 40

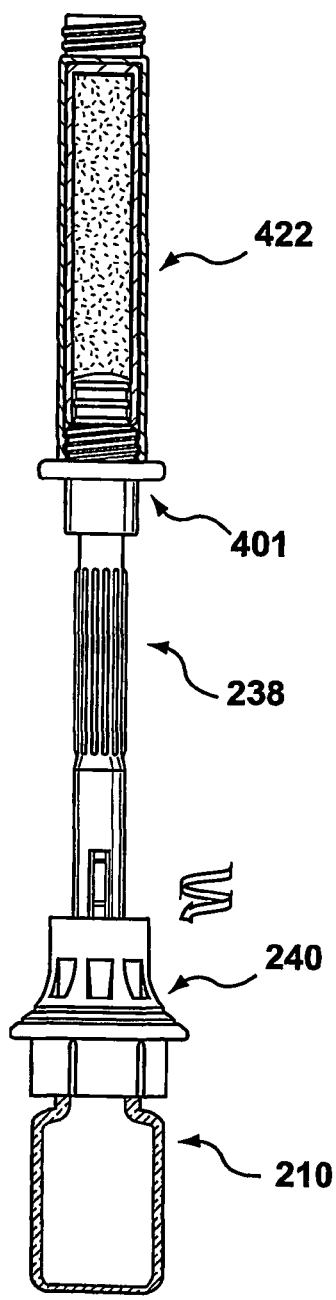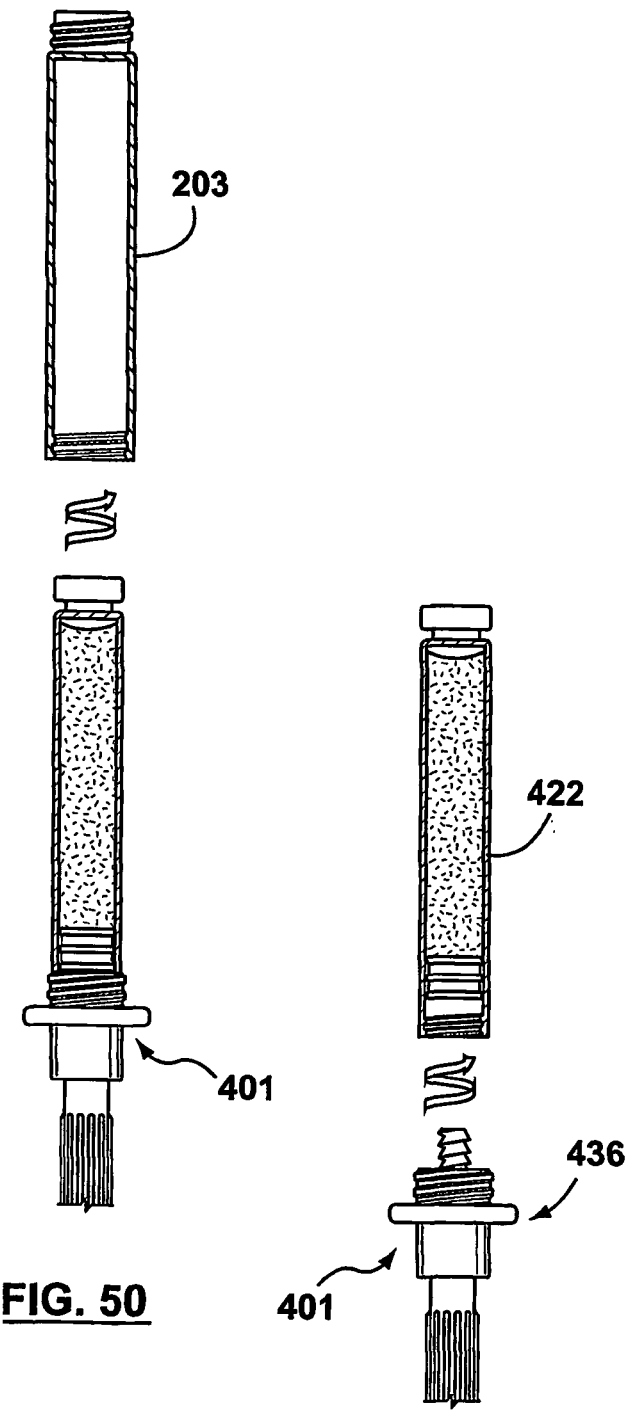
FIG. 49  FIG. 50  FIG. 51

_US 7,736,353 B2_

PHARMACEUTICAL DELIVERY SYSTEMS AND METHODS FOR USING SAME

FIELD OF THE INVENTION

The present invention generally relates to pharmaceutical delivery systems, and to methods for using same. More specifically, it relates to an assembly for transferring one or more components of a pharmaceutical composition from a pharmaceutical vial to a syringe or vice versa.

BACKGROUND OF THE INVENTION

Traditionally, a syringe is filled manually by aspirating a liquid pharmaceutical component from a pharmaceutical vial having a neck with a penetrable closure into the syringe through a needle that penetrates the penetrable closure. The method of manually filling the syringe typically includes the following steps: (a) drawing air into the body of the syringe by pulling the syringe's plunger away from the needle end of the syringe until the volume of air in the body approximately equals the volume of pharmaceutical component to be loaded into the syringe; (b) carefully aligning the needle with the vial's penetrable closure and inserting the needle through the penetrable closure into the vial; (c) inverting the vial and forcing the air from the body of the syringe into the vial by advancing the syringe's plunger; (d) withdrawing the plunger to draw out the desired volume of the pharmaceutical component into the syringe; and (e) removing the needle from the vial.

This method suffers from various disadvantages. Firstly, the user is exposed to the unprotected needle tip, which can result in accidental stabbings or prickings to the user. Secondly, if the user wishes to draw a large volume of the pharmaceutical component into the syringe (e.g., 10 cc) an equivalent volume of air must be forced into the vial. This can increase the pressure in the pharmaceutical vial to the point where the pharmaceutical component may spray through the puncture point made by the needle in the penetrable seal and onto the user. These accidents are particularly dangerous if the pharmaceutical component is unsafe to the user, for example toxic oncology pharmaceuticals. Thirdly, the sterility of the needle may be compromised during the process of transferring the pharmaceutical component from the vial to the syringe.

Additionally, many pharmaceutical preparations must be distributed and stored as two or more separate components (commonly a solid lyophilized component and a liquid component). The two components are mixed just prior to administration. In the case of a solid and liquid component, the solid component is reconstituted by: (a) providing a first solid component packaged in a pharmaceutical vial having a neck closed by a penetrable closure; (b) providing a second liquid component in a syringe; (c) injecting the second liquid component into the vial through the penetrable closure; (d) swirling the vial impaled on the syringe to dissolve, dilute or suspend the first solid component in the second component; and (e) aspirating the combined components back into the syringe. Alternatively, the two or more components may be liquid and require mixing just prior to administration. The mixing may be accomplished in an analogous manner. These methods suffer from many of the disadvantages described above.

SUMMARY OF THE INVENTION

The present invention provides for an assembly for transferring a fluid between a vessel having a body with an open end and a slidable piston positioned within the body through the open end and a vial having a penetrable seal, the assembly comprising:

a) a housing having first and second open ends and a bore extending between the first and second open ends, the housing being removably connectable to the piston;

b) a conduit having first and second ends and first and second apertures adjacent to the first and second ends, respectively, the conduit longitudinally slidable within the bore between a retracted position in which the first aperture is positioned within at least one of the housing and the piston when the housing is connected to the piston, and an activated position in which the first aperture protrudes through the piston into the body of the vessel when the housing is connected to the piston;

c) a vial socket assembly having a vial socket for receiving and engaging at east a portion of the vial including the penetrable seal and a hollow piercing member having a first open end in fluid communication with the conduit and a second open end for piercing the penetrable closure, the vial socket assembly moveable longitudinally relative to the housing in concert with the conduit, whereby advancing the vial socket assembly longitudinally towards the housing advances the conduit from the retracted position to the activated position to fluidly connect the vessel and the vial.

In one aspect of the invention, the first end of the conduit has a piercing member and the aperture is an opening adjacent to a tip of the piercing member.

In another aspect of the invention, the assembly further comprises a hub disposed between the second end of the conduit and the first open end of the hollow piercing member.

In another aspect of the invention, the vial socket assembly further comprises a post releasably receivable within the hub.

In another aspect of the invention, the hub forms a female luer slip and the post forms a male luer slip that is releasably receivable in the female luer slip.

In another aspect of the invention, the bore of the housing has a first portion, a second portion adjacent to the first portion, and a shoulder formed between the first and second portions.

In another aspect of the invention, the assembly further comprises a resilient biasing member positioned between the shoulder and the hub to bias the conduit into the retracted position.

In another aspect of the invention, the resilient biasing member is a spring.

In another aspect of the invention, the first end of the conduit has a blunt end and the first aperture is an opening on a sidewall of the conduit.

In another aspect of the invention, the second end of the conduit is integrally connected to the vial socket assembly.

In another aspect of the invention, the assembly further comprises a retaining member in the vial socket for retaining a vial within the vial socket.

In another aspect of the invention, the retaining member comprises an annular ridge on an interior surface of the vial socket, the annular ridge having a smaller diameter than the diameter of the vial socket.

In another aspect of the invention, the retaining member comprises a plurality of retaining latches provided in the vial socket.

In another aspect of the invention, the vessel is a syringe having a neck with a needle mount for removably mounting a needle thereon and a flange adjacent the open end.

In another aspect of the invention, the assembly further comprises a piston backstop positioned adjacent the flange, the piston backstop having a retaining member for retaining the housing in spaced relation from the piston.

In another aspect of the invention, the piston backstop is shaped and sized to slidably receive the housing.

In another aspect of the invention, the piston backstop is removably connectable to the flange.

In another aspect of the invention, the syringe is glass.

In another aspect of the invention, the assembly further comprises a sheath assembly positioned over the neck of the syringe, the sheath assembly removably connectable to the piston backstop.

In another aspect of the invention, the syringe is plastic and the piston backstop is integrally molded with the syringe.

In another aspect of the invention, the vessel is a cartridge having a neck with a penetrable closure and a cap to retain the penetrable closure thereon.

In another aspect of the invention, the assembly further comprises a sheath assembly positioned over the neck of the cartridge and a piston backstop removably connectable to the sheath assembly, the piston backstop having a retaining member for retaining the housing in spaced relation from the piston.

In another aspect of the invention, the assembly further comprises a piston backstop positioned adjacent the open end of the cartridge, the piston backstop having a retaining member for retaining the housing in spaced relation from the piston.

In another aspect of the invention, the cartridge is plastic and the piston backstop is integrally molded with the cartridge.

The present invention also provides for a piston backstop for use with a syringe having a body with an open end and a slidable piston positioned within the body through the open end, the piston backstop comprising:

a) a bottom plate having an aperture sized to permit the passage of a plunger rod therethrough;

b) a pair of opposing generally coplanar top plate extensions spaced apart to permit the passage of the plunger rod therethrough;

c) a pair of side walls connecting the bottom plate to the respective top plate extensions thereby creating a pair of gaps between the bottom plate and the respective top plate extensions, the gaps sized to receive a flange of a syringe therein;

d) a retaining member for retaining the plunger rod in spaced relation from the piston.

In another aspect of the invention, the retaining member is an internal thread in the aperture to matingly engage with an external thread on a plunger rod.

In another aspect of the invention, the piston backstop further comprises a collar extending from the aperture in the bottom plate.

In another aspect of the invention the retaining member is an internal thread in the collar to matingly engage with an external thread on a plunger rod.

BRIEF DESCRIPTION OF THE DRAWINGS

For a better understanding of the present invention and to show more clearly how it may be carried into effect, reference will now be made, by way of example, to the accompanying drawings which illustrate various embodiments of the invention and in which:

FIGS. 2-7 illustrate successive stages in the deployment of the pharmaceutical transfer assembly as shown in FIG. 1 to reconstitute a multi-component pharmaceutical according to a further aspect of the invention;

FIGS. 8-13 illustrate successive stages in the deployment of the pharmaceutical transfer assembly as shown in FIG. 1 to reconstitute a multi-component pharmaceutical according to a further aspect of the invention;

FIGS. 14-19 illustrate successive stages in deployment of the pharmaceutical transfer assembly as shown in FIG. 1 to transfer a fluid pharmaceutical component from a prepackaged pharmaceutical vial to a syringe according to a further aspect of the invention;

FIGS. 32-37 illustrate successive stages in the deployment of the pharmaceutical transfer assembly of FIG. 27 to reconstitute a multi-component pharmaceutical according to a further aspect of the present invention;

FIG. 38 is an exploded cross-sectional view of a syringe according to a further aspect of the present invention;

FIG. 39 is a cross-sectional view of the syringe of FIG. 39 in a first position;

FIG. 40 is a cross-sectional view of the syringe of FIG. 39 in a second position.

FIGS. 44-51 illustrate successive stages in the deployment of the pharmaceutical transfer assembly of FIG. 43 to reconstitute a multi-component pharmaceutical according to a further aspect of the present invention;

DETAILED DESCRIPTION OF THE INVENTION

The pharmaceutical transfer assemblies described herein are adapted to be used with a standard pharmaceutical vial and a standard syringe or slightly modified versions thereof. These standard devices are well known in the art, but examples will be described here briefly.

Figure 1:
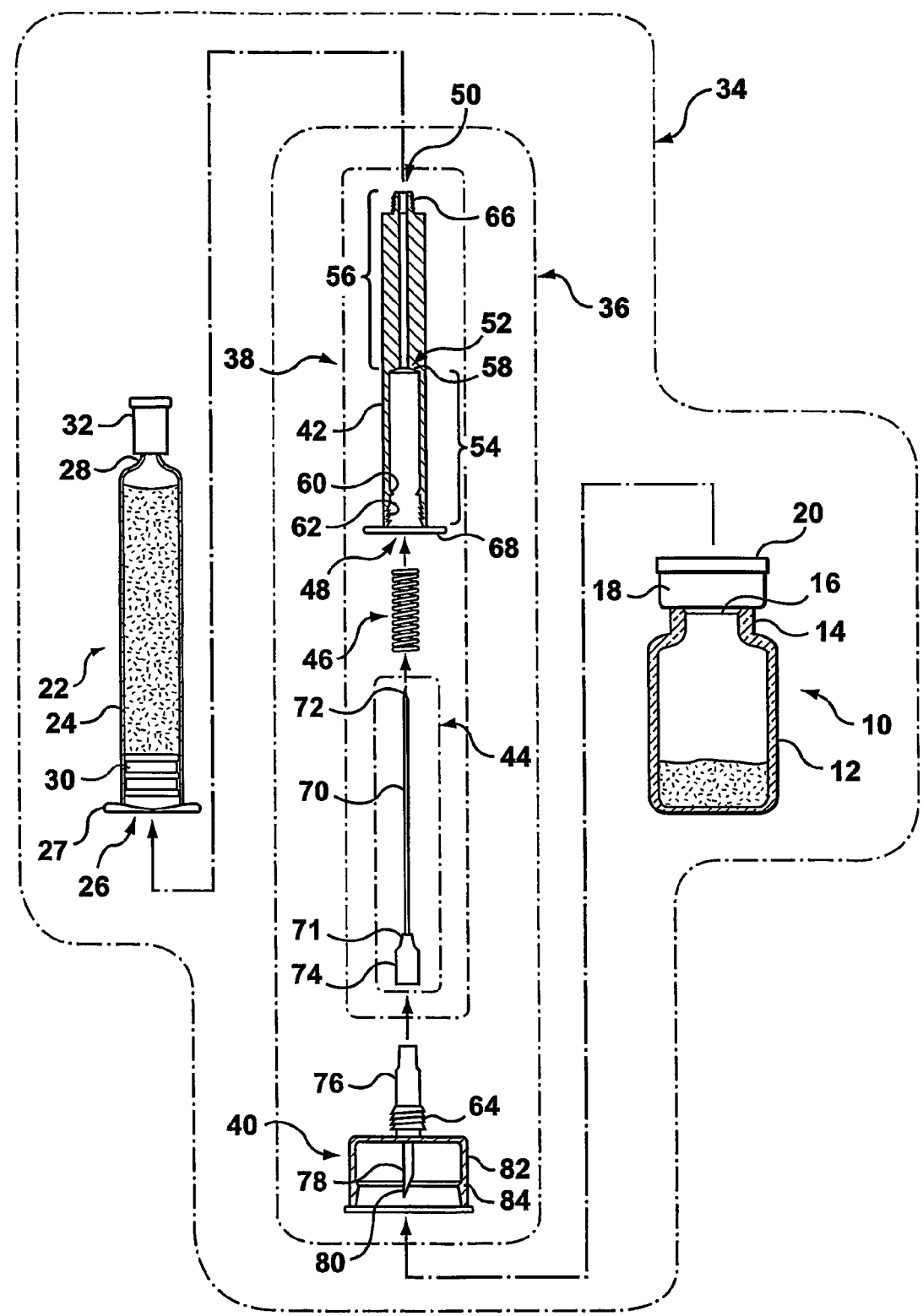
FIG. 1 is an exploded side elevational view of a pharmaceutical delivery system including a pharmaceutical transfer assembly according to one aspect of the present invention.
Figures 2, 3:
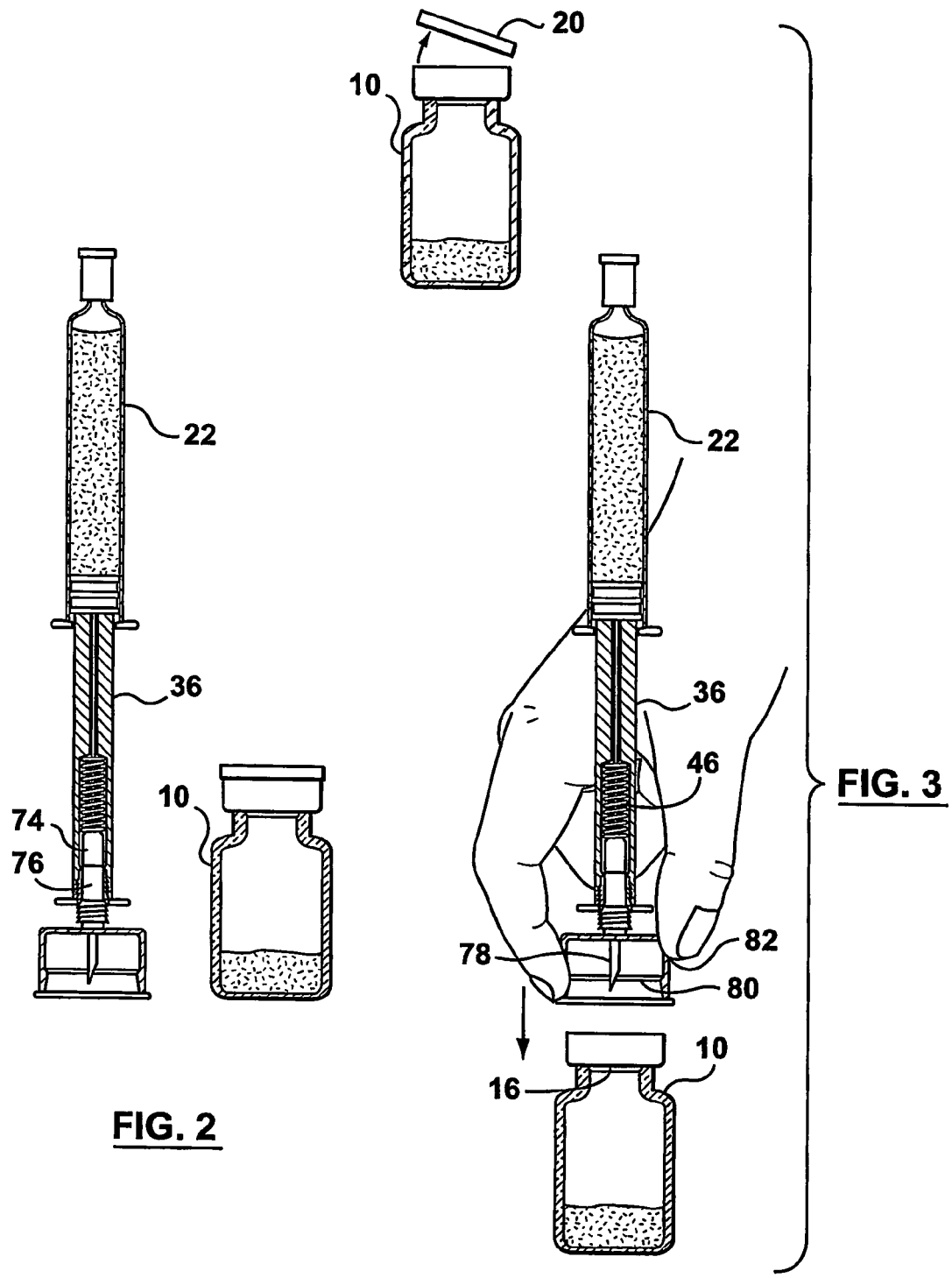

As best seen in FIG. 1, a standard pharmaceutical vial 10 generally has a vial body 12, a neck 14 of a reduced diameter compared with the body 12, a penetrable closure 16 made of an elastomeric material (e.g. rubber), a cap 18 to hold the penetrable closure 16 onto the pharmaceutical vial 10, and a cover 20 to protect the integrity of the penetrable closure 16 before use.

Still referring to FIG. 1, a standard syringe 22 may be a glass syringe having a syringe body 24 being open at one end 26 and having a neck 28 at the opposite end. A piston 30 is lodged in the syringe body 24 from the open end 26, the piston 30 being provided with means (not shown) by which a standard detachable plunger rod (not shown) may be secured to the piston 30. The open end 26 of the syringe body 24 is provided with a flange 27. The neck 28 of the syringe body 24 has a needle mount (which in the illustrated embodiment is a standard needle coupling or "luer lock" comprising a conical spigot (not shown) with a central passage communicating with the syringe body 24 surrounded by a cylindrical sleeve (not shown) having an internal thread (not shown)). The neck 28 of the syringe body 24 is sealed with a tip cap 32 made of an elastomeric material (e.g. rubber).

Still referring to FIG. 1, a pharmaceutical delivery system made in accordance with one aspect of the present invention is shown generally at 34. The pharmaceutical delivery system 34 generally comprises the syringe 22 pre-filled with a first fluid pharmaceutical component, a pharmaceutical transfer assembly shown generally at 36, and the pharmaceutical vial 10 containing a second pharmaceutical component. It is understood that the second pharmaceutical component may be either a fluid or a solid (e.g. lyophilized powder). The pharmaceutical transfer assembly 36 generally comprises a detachable needle transfer plunger rod shown generally at 38, and a vial socket assembly shown generally at 40.

The detachable needle transfer plunger rod 38 may be of any suitable size and shape. In one aspect of the invention, the detachable needle transfer plunger rod 38 has the same dimensions as a standard detachable plunger rod as is well known by a person skilled in the syringe art. The detachable needle transfer plunger rod 38 generally comprises a housing 42, a needle hub assembly 44, and a resilient biasing member 46.

The housing 42 has a first open end 48, a second open end 50 opposite open end 48, and a bore 52 disposed between the first and second open ends 48, 50. The bore 52 is appropriately sized and shaped to receive the needle hub assembly 44 and the resilient biasing member 46, which will be described in more detail below. The bore 52 generally has a first portion 54 and an adjacent second portion 56. The first portion 54 has a larger diameter than the second portion 56, and an inner annular shoulder 58 is formed at the juncture between the first and second portions 54, 56. There is an annular detent 60 in the first portion 54 to provide a snap fit connection to secure the needle hub assembly 44 in a retracted or "inactivated" position while not in use, as will be subsequently described.

There is an internal thread 62 in the first portion 54 of the bore 52 that cooperates with an external thread 64 on the vial socket assembly 40 to securely lock the vial socket assembly 40 onto the needle transfer plunger rod 38 thereby advancing the needle hub assembly 44 into an advanced or "activated" position, as will be subsequently described. There is an external thread 66 on the second open end 50 of the housing 42 that cooperates with an internal thread (not shown) contained within the piston 30 to permit the needle transfer plunger rod 38 to be connected to the syringe 22. The first open end 48 of the housing 42 preferably has a finger flange 68 with a central bore (not shown) to aid in gripping the pharmaceutical transfer assembly 36 during operation.

The needle hub assembly 44 generally comprises a conduit (which in the illustrated embodiment is a first hollow piercing member 70 having a tip 72) connected to a needle hub 74. The first hollow piercing member 70 may be any suitable device well known in the art, and in one embodiment is a hollow needle such as a standard cannula. The needle hub assembly 44 is adapted for longitudinal movement within the bore 52 between a retracted or "unactivated" position (as seen in FIGS. 2-3, 7, 8-9, 12, 14-15, 19) and an advanced or "activated" position (as seen in FIGS. 4-6, 10-12, 16-18). As will be described more particularly below, in the retracted position, the tip 72 of the first hollow piercing member 70 is fully contained within the second portion 56 of the bore 52 of the housing 42. In the advanced position, the tip 72 of the first hollow piercing member 70 protrudes past the second portion 56 of the bore 52 of the housing 42 and penetrates the piston 30. The needle hub 74 has a female luer slip fitting to permit receipt of a post 76 of the vial socket assembly 40. The needle hub 74 and the post 76 act to hold the vial socket assembly 40 to the needle transfer plunger rod 38 initially when the needle hub assembly 44 is in the retracted or "inactivated" position.

The resilient biasing member 46 may be any suitable device well known in the art, and in one embodiment is a compressible spring. The resilient biasing member 46 is adapted to fit within the first portion 54 of the bore 52 between a surface 71 of the needle hub 74 and the annular shoulder 58. While the needle hub assembly 44 is in the retracted or "unactivated" position, the resilient biasing member 46 is at rest (e.g. no force is being applied to or by the resilient biasing member 46 by the needle hub 74). While the needle hub assembly 44 is in the advanced or "activated" position, the resilient biasing member 46 is compressed against the annular shoulder 58 by the needle hub 74 (e.g., a force is being applied to the resilient biasing member 46). The main purpose of the resilient biasing member 46 is to retract the needle hub assembly 44 back to the original retracted or "unactivated" position after the fluid transfer has been completed and the vial socket assembly 40 has been removed from the needle transfer plunger rod 38, as will subsequently be described.

The vial socket assembly 40 generally comprises the post 76, a second hollow piercing member 78 having a tip 80, and a vial socket 82. The post 76 has a male luer slip fitting that permits coupling between the post 76 and the needle hub 74 while the pharmaceutical transfer assembly is in the retracted or "inactivated position". The second hollow piercing member 78 may be any suitable device well known in the art, and in one embodiment is a hollow needle such as a standard spike. The vial socket 82 is appropriately sized and shaped to receive a standard pharmaceutical vial 10 having the penetrable closure 16 and the cap 18, described above. Preferably, the vial socket 82 has a retaining member (which in the illustrated embodiment is an inner annular ridge 84 of smaller dimension than the vial socket 82 for positively engaging the cap 18 of the vial 10 once it is fully inserted into the vial socket 82 (as shown in FIGS. 2-3, 8-9, and 14-15)).

Referring now to FIGS. 2-7, the successive stages in the deployment of a pharmaceutical transfer assembly 36 as shown in FIG. 1 to reconstitute a first fluid pharmaceutical component from a pre-filled syringe 22 with a second pharmaceutical component from a pharmaceutical vial 10 are shown. It is understood that the second pharmaceutical component contained within the pharmaceutical vial 10 may be either a fluid or a solid (e.g. lyophilized powder).

Still referring to FIGS. 2-7, the method for deploying the pharmaceutical transfer assembly 36 is described in detail below. Step (a) involves screwing external thread 66 into the internal thread (not shown) within piston 30 and inserting the post 76 of the vial socket assembly 40 into the needle hub 74 to create the assembly shown in FIG. 2. Step (b) involves removing the cover 20 of the pharmaceutical vial 10 (see FIG. 3). Step (c) involves inserting and snap fitting the pharmaceutical vial 10 into the vial socket 82 of the vial socket assembly 40 such that the tip 80 of the second hollow piercing member 78 penetrates the penetrable closure 16 on the pharmaceutical vial 10 (see FIG. 3). It is understood that step (a) can be performed first followed by steps (b) and (c) in that order, or steps (b) and (c) can be performed first in that order followed by step (a).

After completing steps (a), (b), and (c), step (d) involves advancing both the pharmaceutical vial 10 and the vial socket assembly 40 forward towards the syringe 22 and locking the vial socket assembly 40 into place by screwing the external thread 64 into the internal thread 62 of the plunger rod housing 42. This, in turn, advances the tip 72 of the first hollow piercing member longitudinally within the bore 52 of the housing 42 from the retracted position to the advanced position wherein the tip 72 of the first hollow piercing member 70 penetrates the piston 30. With both tip 72 and tip 80 having pierced their respective items, this creates fluid communication between the pharmaceutical vial 10 and the syringe 22 (see FIG. 4).

Step (e) involves advancing the syringe body 24 longitudinally towards the pharmaceutical vial 10. This moves piston 30 relative to neck 28 to force the fluid within the syringe body 24 into and through the needle assembly 44 and through the vial socket assembly 40 to inject the first fluid pharmaceutical component into the pharmaceutical vial 10 (see FIG. 5). Step (f) involves swirling the pharmaceutical delivery system 34 to dissolve, dilute or suspend the first fluid pharmaceutical component into the second pharmaceutical component.

Figure 6:
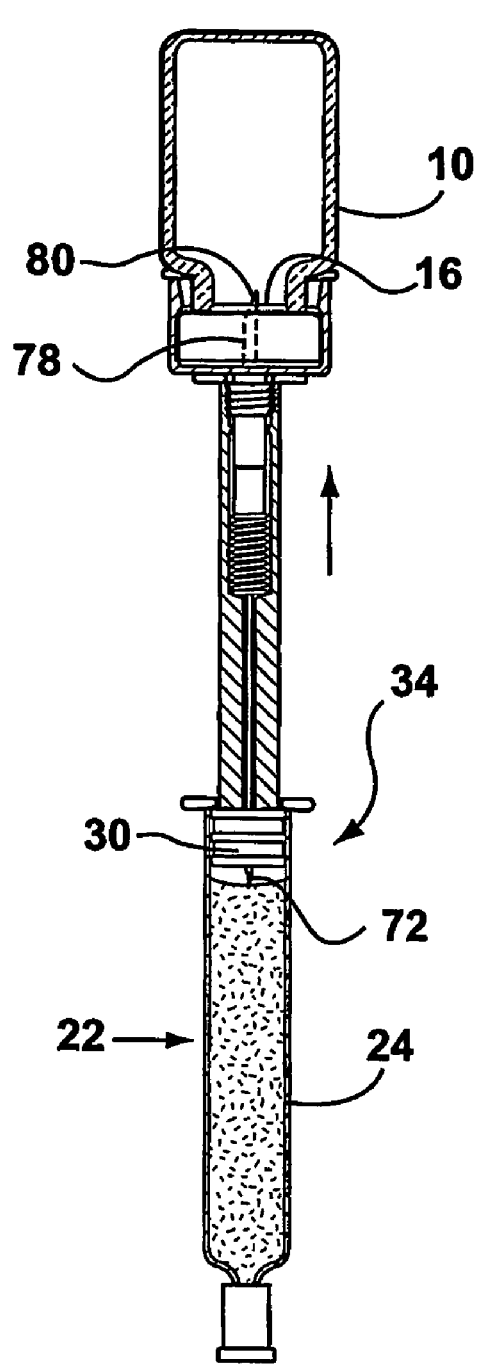

Step (g) involves inverting the pharmaceutical delivery system 34 and withdrawing the syringe body 24 longitudinally away from the pharmaceutical vial 10 to aspirate the now mixed contents of the pharmaceutical vial 10 back into the syringe 22 (see FIG. 6).

Figure 7:
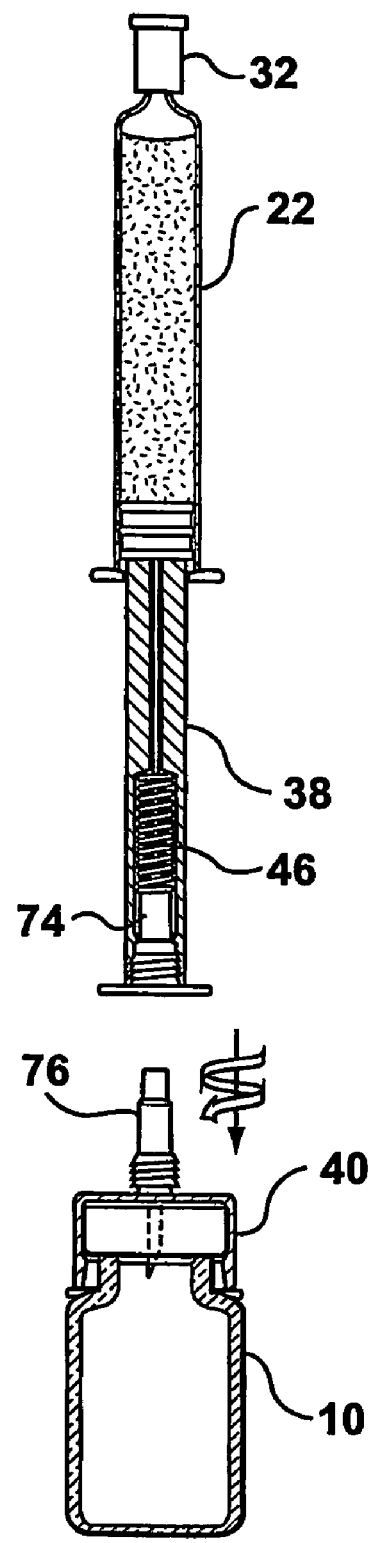

Step (h) involves detaching the vial socket assembly 40 from the needle transfer plunger rod 38 (by unthreading the two and pulling the post 76 of the vial socket assembly 40 out of the needle hub 74) to provide a filled syringe 22 ready for use (see FIG. 7). To use the filled syringe the tip cap 32 is removed and a needle (not shown) attached. The needle transfer plunger rod 38 forms the plunger to discharge the mixed pharmaceutical from the syringe 22.

It is understood by a person skilled in the art that once the vial socket assembly 40 is detached from the needle transfer plunger rod (by unthreading the two), the resilient biasing member 46 retracts the first hollow piercing member back to the retracted or "inactivated" position. As such, the piston 30 reseals to prevent fluid communication between the syringe 22 and the needle transfer plunger rod 38. Accordingly, when the syringe 22 is used to deliver the reconstituted multi-component pharmaceutical to a patient or iv line, the needle transfer plunger rod 38 is depressed in a conventional way.

Referring now to FIGS. 8-13, the successive stages in the deployment of a pharmaceutical transfer assembly 36 as shown in FIG. 1 to reconstitute a first pharmaceutical component from a prepackaged syringe 22 with a second fluid pharmaceutical component from a prepackaged pharmaceutical vial 10 are shown. It is understood that the first pharmaceutical component contained within the syringe 22 may be either a fluid or a solid (e.g., lyophilized powder).

Figures 8, 9:
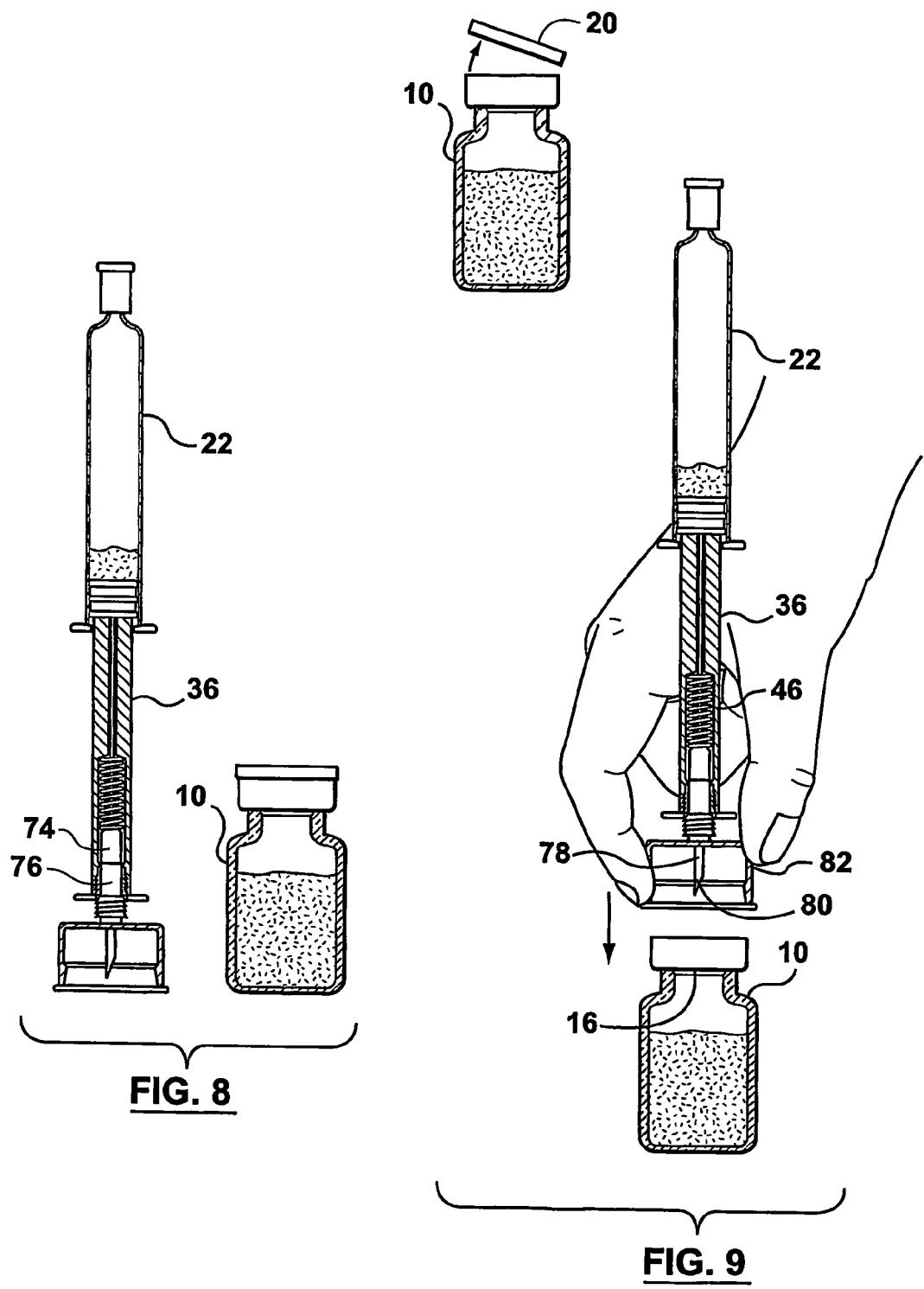
Figure 10:
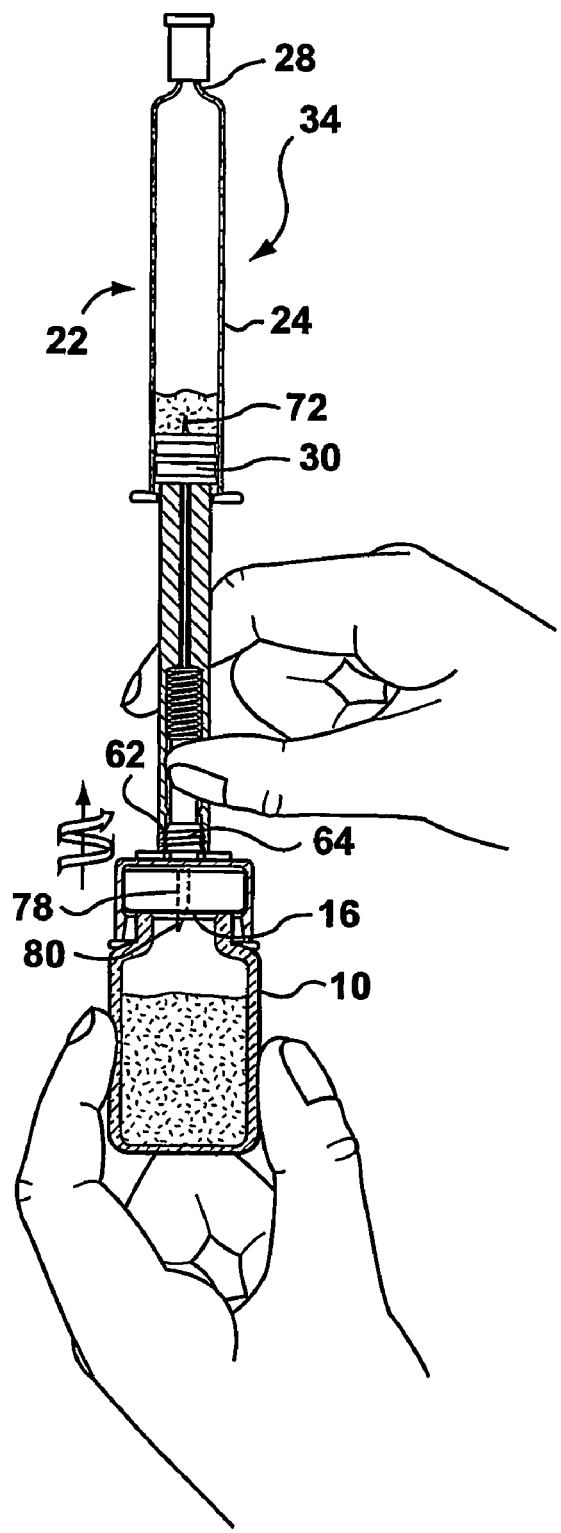
Figure 11:
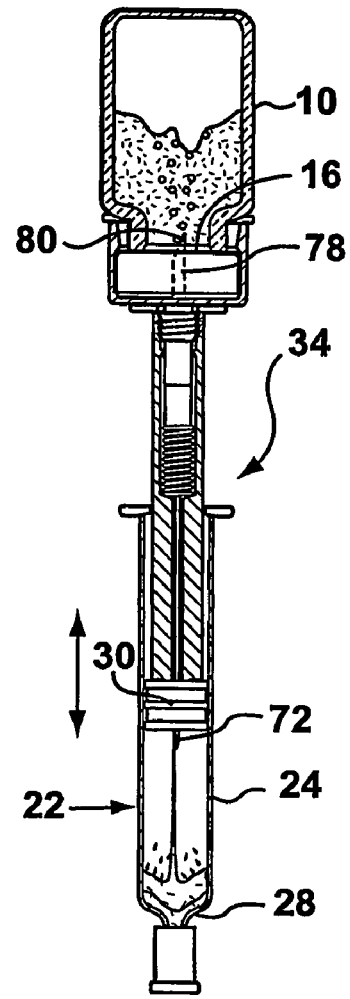
Figure 14:
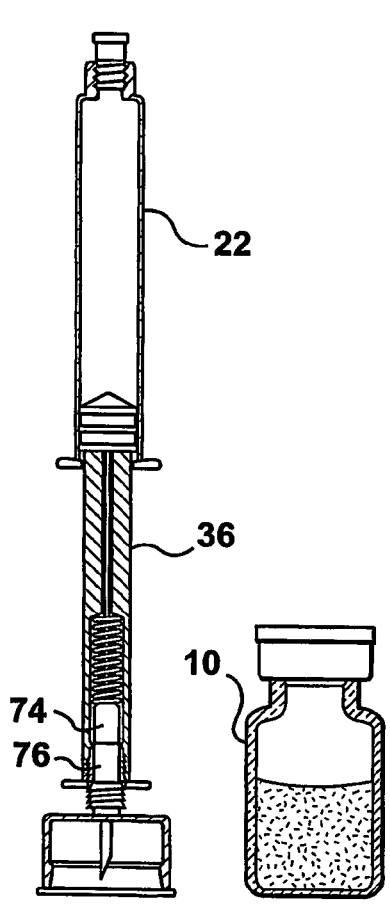

Still referring to FIGS. 8-13, the method for deploying the pharmaceutical transfer assembly 36 is described in detail below. Step (a) involves screwing external thread 66 into the internal thread (not shown) within piston 30 and inserting post 76 of the vial socket assembly 40 into the needle hub 74 to create the assembly shown in FIG. 8. Step (b) involves removing the cover 20 of the pharmaceutical vial 10 (FIG. 9). Step (c) involves inserting and snap fitting the pharmaceutical vial 10 into the vial socket 82 of the vial socket assembly 40 such that the tip 80 of the second hollow piercing member 78 penetrates the penetrable closure 16 on the pharmaceutical vial 10 (see FIG. 9). It is understood that step (a) can be performed first followed by steps (b) and (c) in that order, or steps (b) and (c) can be performed first in that order followed by step (a).

After completing steps (a), (b), and (c), step (d) involves advancing both the pharmaceutical vial 10 and the vial socket assembly 40 forward towards the syringe 22 and locking the vial socket assembly 40 into place by screwing the external thread 64 into the internal thread 62 of the plunger rod housing 42. This, in turn, advances the tip 72 of the first hollow piercing member 70 longitudinally within the bore 52 of the housing 42 from the retracted position to the advanced position wherein the tip 72 of the first hollow piercing member 70 penetrates the piston 30. With both tip 72 and tip 80 having pierced their respective items, this creates fluid communication between the pharmaceutical vial 10 and the syringe 22 (see FIG. 10).

Step (e) involves inverting the pharmaceutical delivery system 30 and advancing the syringe body 22 longitudinally towards the pharmaceutical vial 10. This moves piston 30 relative to neck 28 to force the air within the syringe body 24 into and through the needle assembly 44 and through the vial socket assembly 40 to aspirate the air into the pharmaceutical vial 10. Step (f) involves withdrawing the syringe body 24 away from the pharmaceutical vial to aspirate the second, fluid pharmaceutical from the pharmaceutical vial 10 into the syringe 22 (see FIG. 11). Step (g) involves swirling the pharmaceutical delivery system 34 to dissolve, dilute or suspend the second, fluid pharmaceutical component into the first pharmaceutical component.

Step (h) involves detaching the vial socket assembly 40 from the needle transfer plunger rod 38 (by unthreading the two and pulling the post 76 of the vial socket assembly 40 out of the needle hub 74) to provide a filled syringe 22 ready for use (see FIG. 13). To use the filled syringe the tip cap 32 is removed and a needle (not shown) attached. The needle transfer plunger rod 38 forms the plunger to discharge the mixed pharmaceutical from the syringe 22.

Referring now to FIGS. 14-19, the successive stages in deployment of the pharmaceutical transfer assembly 36 as shown in FIG. 1 to transfer a fluid pharmaceutical component from a prepackaged pharmaceutical vial 10 to an empty syringe 22 according to a further aspect of the invention are shown.

Figure 15:
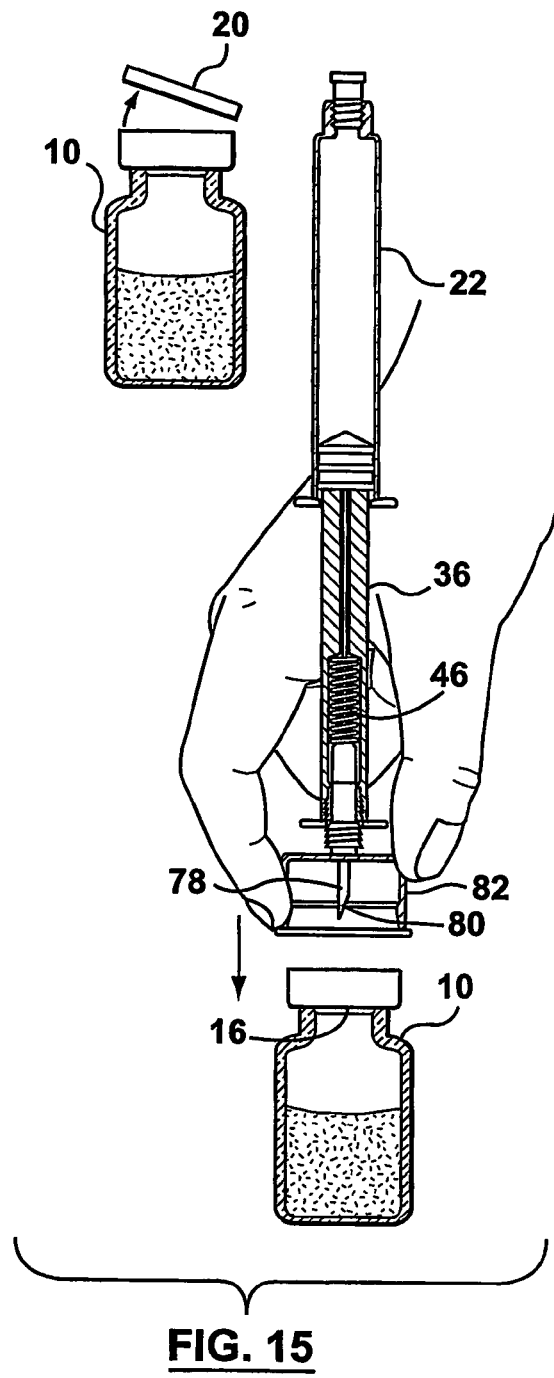
Figure 16:
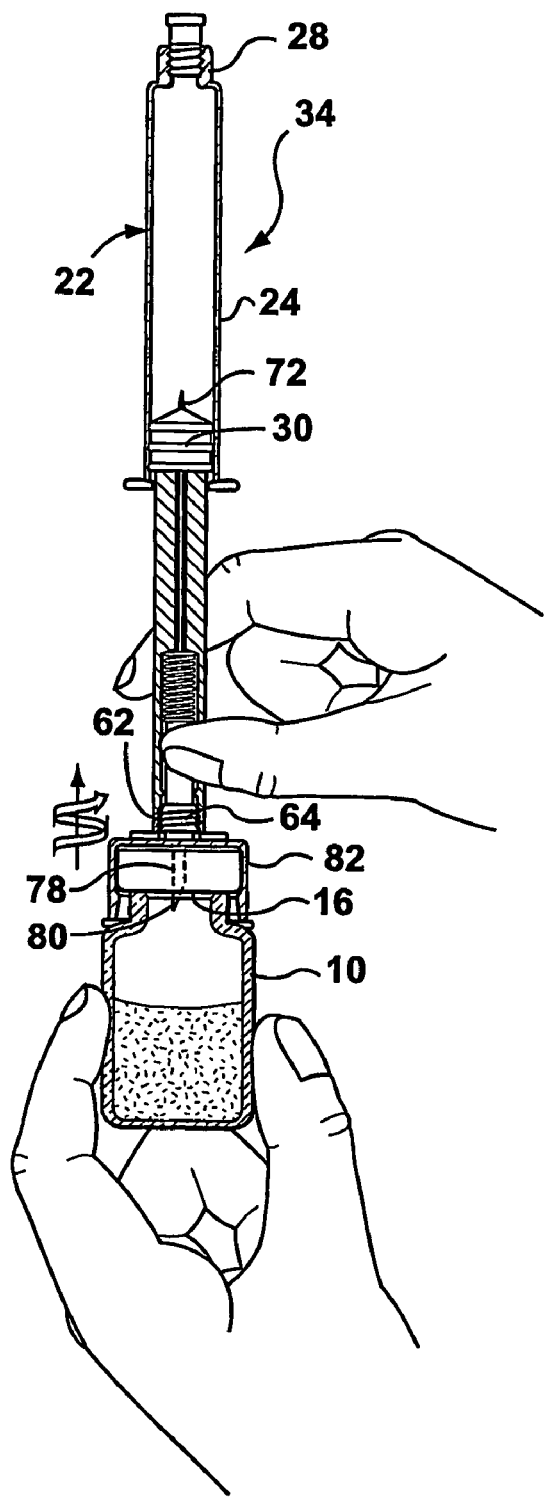
Figure 17:
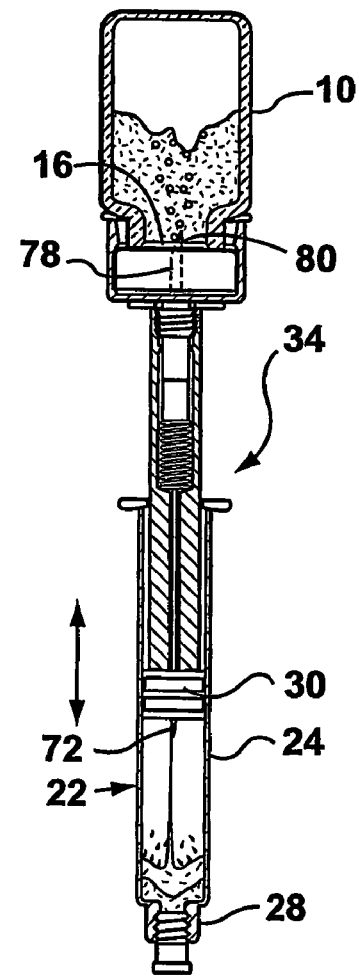

Still referring to FIGS. 14-19, the method for deploying the pharmaceutical transfer assembly 36 is described in detail below. Step (a) involves screwing external thread 66 into the internal thread (not shown) within piston 30 and inserting post 76 of the vial socket assembly 40 into the needle hub 74 to create the assembly shown in FIG. 14. Step (b) involves removing the cover 20 of the pharmaceutical vial 10 (FIG. 15). Step (c) involves inserting and snap fitting the pharmaceutical vial 10 into the vial socket 82 of the vial socket assembly 40 such that the tip 80 of the second hollow piercing member 78 penetrates the penetrable closure 16 on the pharmaceutical vial 10 (see FIG. 15). It is understood that step (a) can be performed first followed by steps (b) and (c) in that order, or steps (b) and (c) can be performed first in that order followed by step (a).

After completing steps (a), (b), and (c), step (d) involves advancing both the pharmaceutical vial 10 and the vial socket assembly 40 forward towards the syringe 22 and locking the vial socket assembly 40 into place by screwing the external thread 64 into the internal thread 62 of the plunger rod housing 42. This, in turn, advances the tip 72 of the first hollow piercing member 70 longitudinally within the bore 52 of the housing 42 from the retracted position to the advanced position wherein the tip 72 of the first hollow piercing member 70 penetrates the piston 30. With both tip 72 and tip 80 having pierced their respective items, this creates fluid communication between the pharmaceutical vial 10 and the syringe 22 (see FIG. 16).

Step (e) involves advancing the syringe body 24 longitudinally towards the pharmaceutical vial 10 to aspirate air into the pharmaceutical vial 10. Step (f) involves inverting the pharmaceutical delivery system 34 to aspirate the fluid pharmaceutical component from the prepackaged pharmaceutical vial 10 into the syringe 22. Step (g) involves detaching the vial socket assembly 40 from the needle transfer plunger rod 38 (by unthreading the two and pulling the post 76 of the vial socket assembly 40 out of the needle hub 74) to provide a syringe 22 ready for use (see FIG. 19). To use the filled syringe the tip cap 32 is removed and a needle (not shown) attached. The needle transfer plunger rod 38 forms the plunger to discharge the transferred fluid from the syringe 22.

Figure 20:
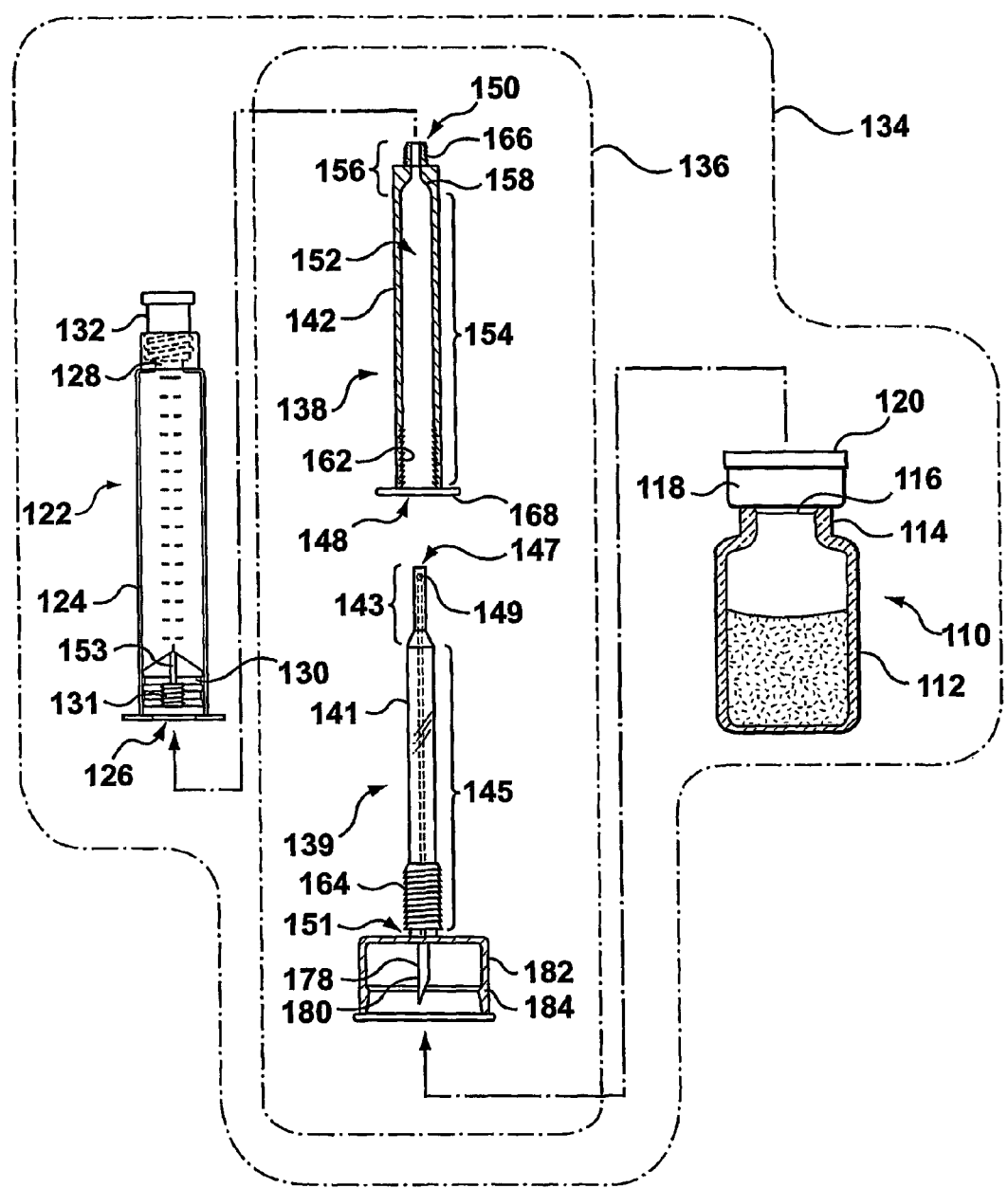
FIG. 20 is an exploded side elevational view of a pharmaceutical delivery system including a pharmaceutical transfer assembly according to a further aspect of the present invention.
Figure 21:
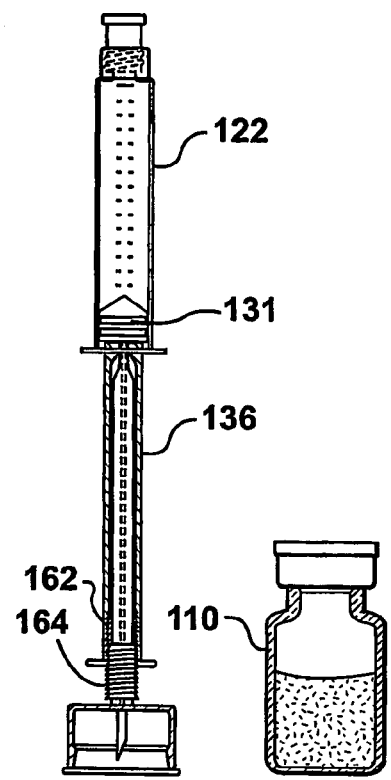
FIGS. 21-26 illustrate successive stages in the deployment of the pharmaceutical transfer assembly of FIG. 20 to transfer a fluid pharmaceutical component from a prepackaged pharmaceutical vial to a syringe according to a further aspect of the invention.

Referring now to FIG. 20, a pharmaceutical delivery system made in accordance with another aspect of the present invention is shown generally at 134. The pharmaceutical delivery system 134 generally comprises an empty syringe 122, a pharmaceutical transfer assembly shown generally at 136, and a pharmaceutical vial 110 containing a fluid pharmaceutical component. The pharmaceutical transfer assembly 136 generally comprises a detachable plunger rod shown generally at 138, and a transfer tube/vial socket assembly shown generally at 139.

The detachable plunger rod 138 may be of any suitable size and shape. In one aspect of the invention, the detachable plunger rod 138 has the same dimensions as a standard detachable plunger rod as is well known by a person skilled in the syringe art.

The detachable plunger rod generally comprises a housing 142. The housing 142 has a first open end 148, a second open end 150 opposite the first open end 148, and a bore 152 disposed between the first and second open ends 148, 150. The bore 152 is appropriately sized and shaped to receive the transfer tube/vial socket assembly 139, which will be described in more detail below. The bore 152 generally has a first portion 154, and an adjacent second portion 156. The first portion 154 has a larger diameter than the second portion 156. There is an internal thread 162 in the first portion 154 of the bore 152 that cooperates with an external thread 164 on the transfer tube/vial socket assembly 139 to connect the plunger rod 138 to the transfer tube/vial socket assembly 139. These cooperating threads 162, 164 permit axial movement of the transfer tube/vial socket assembly 139 relative to the plunger rod 138. There is an external thread 166 on the second open end 150 of the housing 142 that cooperates with an internal thread 131 contained within the piston 130 to permit the plunger rod 138 to be connected to the syringe 122. The first open end 148 of the housing 142 preferably has a finger flange 168 with a central bore (not shown) to aid in gripping the pharmaceutical transfer assembly 136 during operation.

Figure 23:
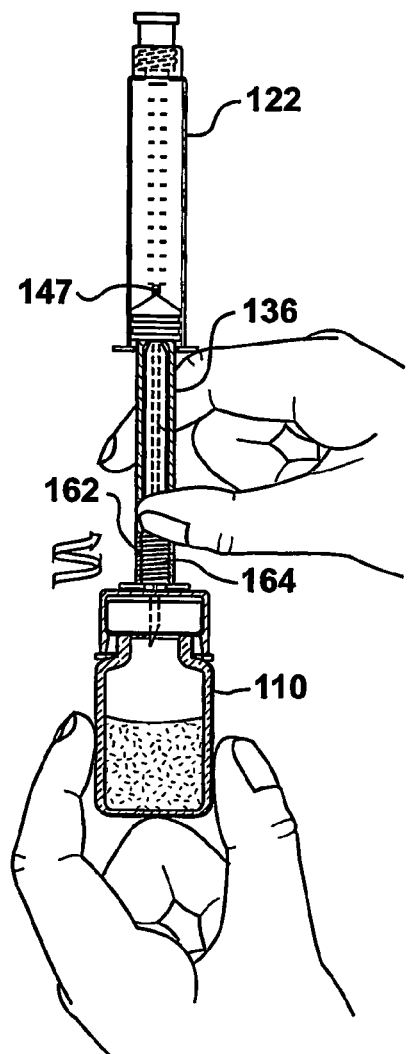
Figure 24:
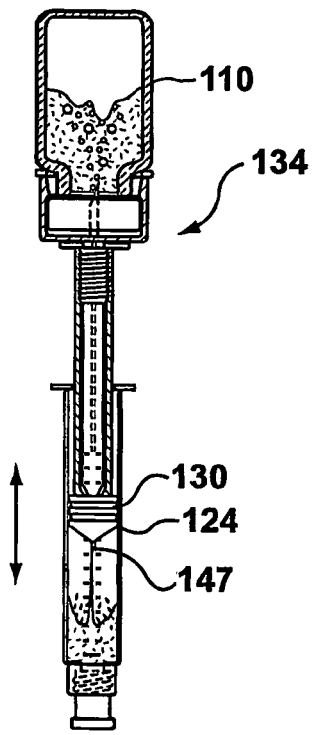
Figure 25:
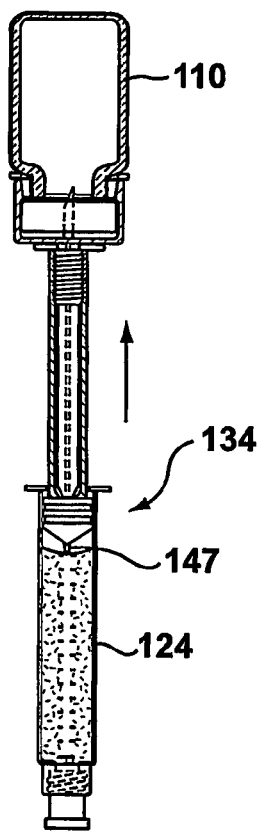

The transfer tube/vial socket assembly 139 generally comprises a conduit (which in the illustrated embodiment is a hollow tube 141) and a vial socket 184. The hollow tube 141 has a first portion 143, and a second portion 145 adjacent the first portion 143. The first portion 143 preferably has a smaller diameter than the second portion 145. The hollow tube 141 has a first end 147, and a second open end 151 opposite the first end 147. The first end 147 preferably has a blunt tip, and an aperture 149 on a sidewall of the hollow tube adjacent the blunt tip that is in fluid communication with the inside of the hollow tube. The vial socket includes a hollow piercing member 178 having a tip 180. The hollow piercing member 178 may be any suitable device well known in the art, and in one embodiment is a hollow needle such as a standard spike. The second open end 151 of the hollow tube 141 is integrally connected to the vial socket 182, and fluidly connected to the hollow piercing member 178. The vial socket 182 is appropriately sized and shaped to receive a standard pharmaceutical vial 110 having the penetrable closure 116 and the cap 120, described above. Preferably, the vial socket 182 has a retaining member (which in the illustrated embodiment is an inner annular ridge 184 of smaller dimension than the vial socket 182 for positively engaging the cap 120 of the vial 110 once it is fully inserted into the vial socket (as shown in FIGS. 23-25)).

The syringe 122 is slightly modified in this aspect of the invention. In particular, the piston 130 has an aperture 153 with a diameter that is slightly smaller than the diameter of the first portion 143 of the hollow tube 141 to allow snug passage of the hollow tube 141 through the piston 130, as will be subsequently described.

Referring now to FIGS. 21-26, the successive stages in deployment of the pharmaceutical transfer assembly as shown in FIG. 20 to transfer a fluid pharmaceutical component from a prepackaged pharmaceutical vial 110 to a syringe 122 according to a further aspect of the invention are shown.

Still referring to FIGS. 21-26, the method for deploying the pharmaceutical transfer assembly 136 is described in detail below. Step (a) involves screwing external thread 166 into the internal thread 131 within piston 130 and screwing external thread 164 part way into the internal thread 162 within the second portion 154 of the housing 142 to create the assembly shown in FIG. 21. It is understood that before the fluid transfer occurs, the aperture 149 is wholly contained within the aperture 153 in the piston 131 to create a fluid seal.

Figure 22:
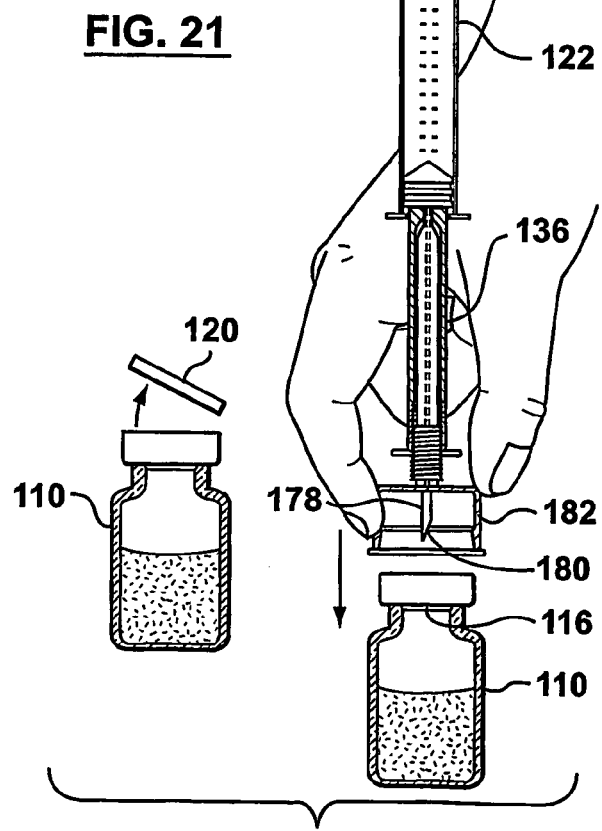

Step (b) involves removing the cover 120 of the pharmaceutical vial 110 (FIG. 22). Step (c) involves inserting and snap fitting the pharmaceutical vial 110 into the vial socket 182 of the transfer tube/vial socket assembly 139 such that the tip 180 of the hollow piercing member 178 penetrates the penetrable closure 116 on the pharmaceutical vial 110 (see FIG. 22).

Step (d) involves screwing the external thread 164 into the internal thread 162 within the second portion 154 of the housing 142 to advance the blunt tip of the hollow tube 141 longitudinally within the bore 152 of the housing 142 from the retracted position to the advanced position wherein aperture 149 in the blunt tip of the hollow tube 141 protrudes through the piston 130 to create fluid communication between the pharmaceutical vial 110 and the syringe 122 (see FIG. 23).

Step (e) involves advancing the syringe body 124 longitudinally towards the pharmaceutical vial 110 to aspirate air into the pharmaceutical vial 10. Step (f) involves inverting the pharmaceutical delivery system 134 to aspirate the fluid pharmaceutical component from the prepackaged pharmaceutical vial 110 into the syringe 122 (see FIG. 24).

Figure 26:
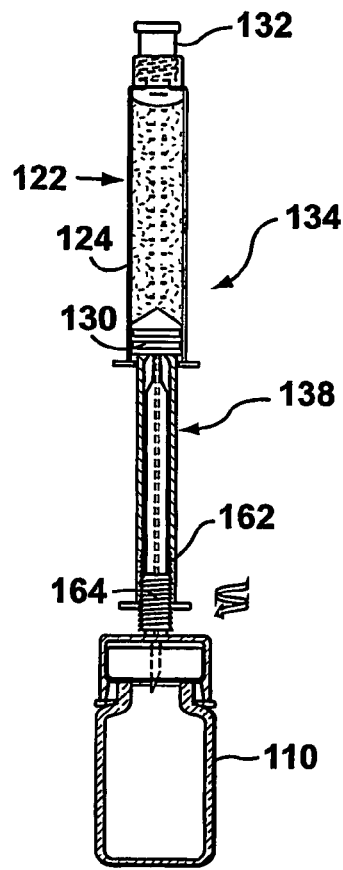

Step (g) involves unscrewing the external thread 164 from the internal thread within the second portion 154 of the housing 142 to retract the blunt tip of the hollow tub 141 longitudinally within the bore 152 of the housing 142 from the advanced position to the retracted position wherein the aperture 149 in the blunt tip of the hollow tube is wholly contained within the piston 130 to create a seal (see FIG. 26). Once the hollow tube has been retracted, the syringe 122 is ready for use. To use the filled syringe 122 the tip cap 132 is removed and a needle (not shown) attached. The plunger rod 138 forms the plunger to discharge the transferred fluid from the syringe 122.

Although the invention has been described in the apparatus and methods in terms of transferring a single dose from the vial 110 to the syringe 122, the apparatus and methods described herein can also be used to transfer a plurality of doses from the vial 110 to the syringe 122 while keeping the pharmaceutical delivery system 134 intact thereby maintaining sterility. After the first dose has been administered, the needle (not shown) is removed from the syringe 122, the tip cap 132 is replaced, and the procedure may be repeated for a second or subsequent dose. The amount drawn in for each repeated dose can be controlled by the degree of movement of the piston 130 within the syringe 122.

Referring now to FIGS. 27-37, a pharmaceutical delivery system made in accordance with another aspect of the present invention is shown generally at 234. The pharmaceutical delivery system 234 has a syringe 222, a, pharmaceutical transfer assembly shown generally at 236, and a pharmaceutical vial 210.

The pharmaceutical transfer assembly 236 has a piston backstop 201, a detachable needle transfer plunger rod shown generally at 238, and a vial socket assembly shown generally at 240.

Optionally, a sheath assembly 203 can be secured over the neck end 228 of the syringe 222 for reasons that will be subsequently described. The sheath assembly 203 has a plastic tip cap 205, and a hard body sheath 207.

Figure 27:
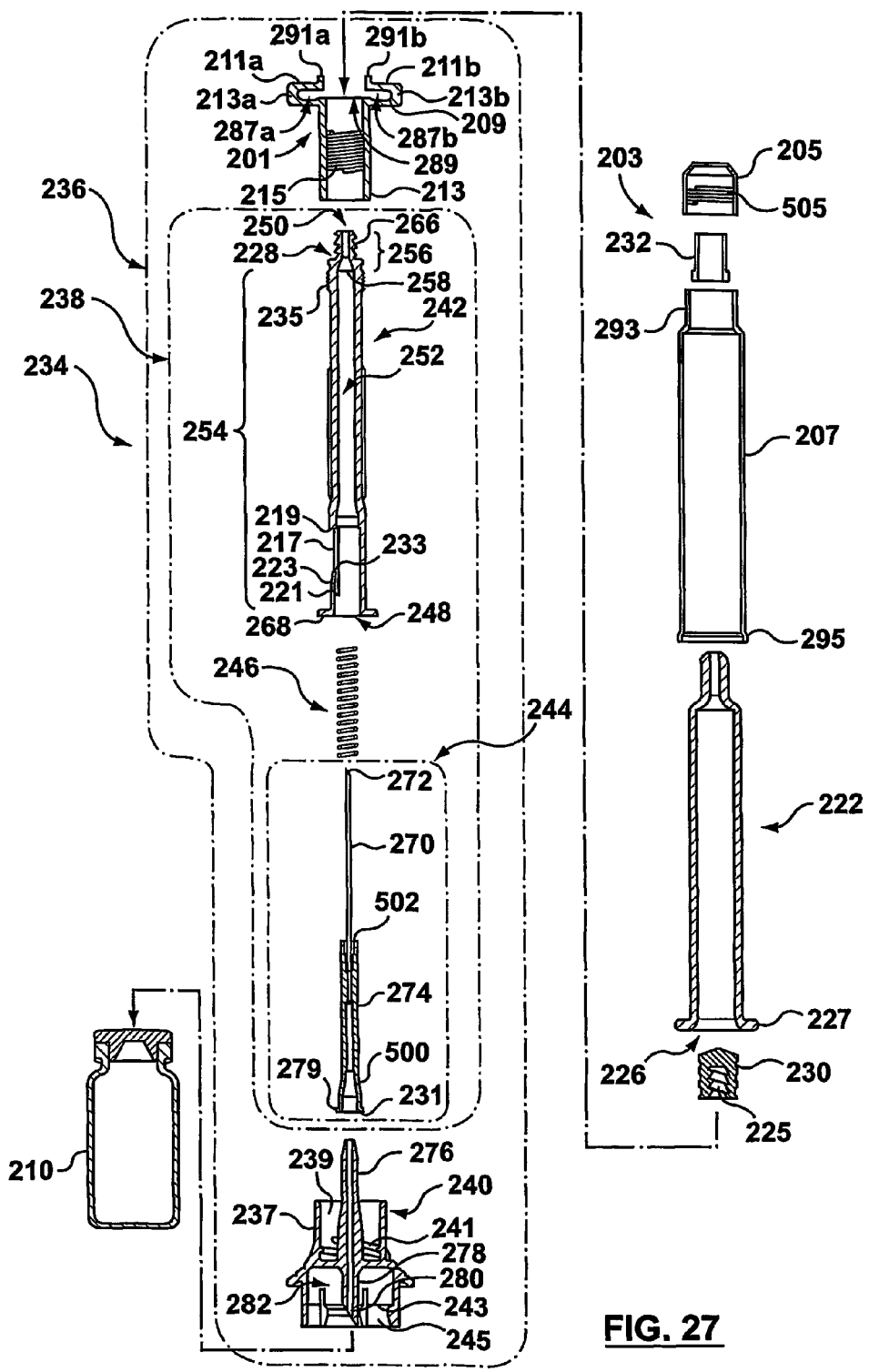
FIG. 27 is an exploded cross-sectional view of a pharmaceutical delivery system including a pharmaceutical transfer assembly according to a further aspect of the present invention.
Figure 41:
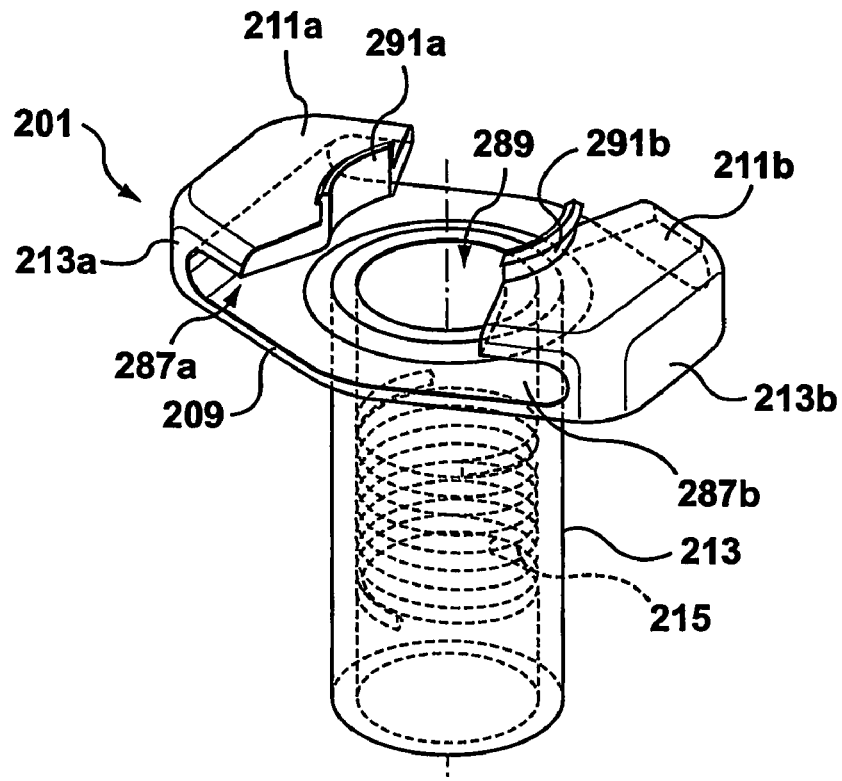
FIG. 41 is a perspective view of a backstop according to a one aspect of the present invention.

Referring now to FIGS. 27 and 41, the piston backstop 201 can be connected to a flange 227 of the syringe 222 to facilitate sterilization of the transfer assembly 236, to prevent accidental activation of the pharmaceutical delivery system 234, and to prevent a piston 230 from being accidentally dislodged from the open end 226 of the syringe 222 as will be described in more detail below. The piston backstop 201 has a bottom plate 209 extending radially from a preferably cylindrical collar 213. The bottom plate 209 has an aperture 289, two top plate extensions 211a, 211b, and two side walls 213a, 213b respectively connecting the bottom plate 209 to the two top plate extensions 211a, 211b. In this arrangement, the bottom plate 209, sidewalls 213a, 213b, and the top plate extensions 211a, 211b form a pair of gaps 287a, 287b that is sized to snugly receive the flange 227 of the syringe 222. Collar 213 has a retaining member (which in this embodiment is an internal thread 215), and an inner diameter that is slightly larger than the outer diameter of the detachable needle transfer plunger rod 238 to permit the needle transfer plunger rod 238 to move axially within the piston stop 201. The piston backstop 201 may have a pair of snaps 291a, 291b positioned on the two top plate extensions 211a to permit attachment of the sheath 207 as will be subsequently described.

The piston backstop 201 can be formed in any conventional manner such as injection molding, and may be made of appropriate plastics, hard rubber materials, or the like. The piston backstop 201 is preferably made from a slightly flexible material to allow it to flex slightly as it is placed about flange 227. Preferably, the piston backstop 201 and preferably the gap is shaped and sized to fit snugly about the flange 227 to ensure that the system does not disassemble during deployment.

The detachable needle transfer plunger rod 238 may be of any suitable size and shape. In one aspect of the invention, the detachable needle transfer plunger rod 238 has the same dimensions as a standard detachable plunger rod as is well known by a person skilled in the art. The detachable needle transfer plunger rod 238 has a housing 242, a needle hub assembly 244, and a resilient biasing member 246.

The housing 242 has a first open end 248, a second open end 250 opposite open end 248, and a bore 252 disposed between the first and second open ends 248, 250. The bore 252 is appropriately sized and shaped to receive therein the needle hub assembly 244 and the resilient biasing member 246, which will be described in more detail below. The bore 252 generally has a first portion 254 and an adjacent second portion 256. The first portion 254 has a larger diameter than the second portion 256, and an inner annular shoulder 258 is formed at the juncture between the first and second portions 254, 256. There is a slot 217 in the first portion 254 of the bore 252 with a top end 219 and a bottom end 221. A latch 223 adjacent the bottom end 221 of the slot 217 supports the needle hub assembly 244 in a retracted or "inactivated" position while not in use, as will be subsequently described. An external thread 266 on the second portion 256 of the housing 242 matingly cooperates with an internal thread 225 contained within the piston 230 to permit the needle transfer plunger rod 238 to be threadedly connected to the piston 230. There is an external thread 235 on the first portion 254 of the housing 242 that matingly cooperates with the internal thread 215 in the piston backstop 201 to permit longitudinal movement of the needle transfer plunger rod 238 relative to the piston backstop 201. The first open end 248 of the housing 242 preferably has a finger flange 268 with a central bore to aid in gripping the pharmaceutical transfer assembly 236 during operation.

The needle hub assembly 244 has a conduit (which in the illustrated embodiment is a first hollow piercing member 270 having a tip 272). The first hollow piercing member is connected to a needle hub 274. The first hollow piercing member 270 may be any suitable device known in the art, and in one embodiment is a hollow needle such as a standard cannula. The needle hub assembly 244 has a size and shape to permit longitudinal movement within the bore 252 between a retracted or "unactivated" position (as seen in FIGS. 29-30, 32-33, and 37) and an advanced or "activated" position (as seen in FIGS. 31, 34-36). As will be described more particularly below, in the retracted position, the tip 272 of the first hollow piercing member 270 is fully contained within the second portion 256 of the bore 252 of the housing 242. In the advanced position, the tip 272 of the first hollow piercing member 270 protrudes past the second portion 256 of the bore 252 of the housing 242 and penetrates completely through the piston 230. The needle hub 274 has a flange 279 having a bottom surface 231 that abuts a top surface 233 of the latch 223 to support the needle hub assembly 244 within the housing 242 while in the retracted or "inactivated" position. The needle hub 274 has a female luer slip 500 fitting to permit receipt of a post 276 of the vial socket assembly 240. The needle hub 274 and the post 276 act to hold the vial socket assembly 240 to the needle transfer plunger rod 238 initially when the needle hub assembly 244 is in the retracted or "inactivated" position.

The resilient biasing member 246 may be any suitable device known in the art, and in one embodiment is a compressible spring. The resilient biasing member 246 is sized and shaped to fit within the first portion 254 of the bore 252 between a surface 502 of the needle hub 274 and the shoulder 258. While the needle hub assembly 244 is in the retracted or "unactivated" position, the resilient biasing member 246 is at rest (e.g. no force is being applied to or by the resilient biasing member 246 by the hub 274). While the needle hub assembly 244 is in the advanced or "activated" position, the resilient biasing member 246 is compressed against the annular shoulder 258 by the hub 274 (e.g., a force is being applied to the resilient biasing member 246). A main purpose of the resilient biasing member 246 is to retract the needle hub assembly 244 to the retracted or "unactivated" position after the fluid transfer has been completed and the vial socket assembly 240 has been removed from the needle transfer plunger rod 238, as will subsequently be described.

The vial socket assembly 240 has a post 276, a collar 237, an annular recess 239 having an internal thread 241, a second hollow piercing member 278 having a tip 280, and a vial socket 282. The post 276 has a male luer slip fitting that permits coupling between the post 276 and the female luer slip fitting 500 on the needle hub 274 while the pharmaceutical transfer assembly 236 is in the retracted or "inactivated position". The flange 268 matingly cooperates with the internal thread 241 in the annular recess 239 to securely connect the vial socket assembly 240 to the needle transfer plunger rod 238. The second hollow piercing member 278 may be any suitable device known in the art, and in one embodiment is a hollow needle such as a spike. The vial socket 282 is appropriately sized and shaped to receive a standard pharmaceutical vial having the penetrable closure and the cap, described above. Preferably, the vial socket 282 has a retaining member (which in the illustrated embodiment is a plurality of retaining latches 243 in the form of an annular ridge around the inner circumference of the vial socket 240, which is divided by a plurality of longitudinal slots 245). The slots 245 permit the vial socket 240 some flexibility to facilitate insertion of the pharmaceutical vial 210. The retaining latches 243 positively engage the cap 220 of the vial 210 once it is fully inserted into the vial socket 240 (as shown in FIGS. 30-31, and 34-36).

The optional sheath assembly 203 generally comprises a plastic cap 205 having an internal thread 505, and a hard body sheath 207 having a corresponding external thread 293 and an annular detent 295. The annular detent 295 snap fits into the snaps 291a, 291b on the top plate extensions of the piston backstop 201 to positively engage the sheath 207 on the piston backstop 201. The sheath assembly 203 protects the syringe 222 from breakage, and also prevents a rubber tip cap 232 from dislodging from the neck end 228 of the syringe 222 during both transport and deployment of the pharmaceutical transfer system 234.

Figure 28:
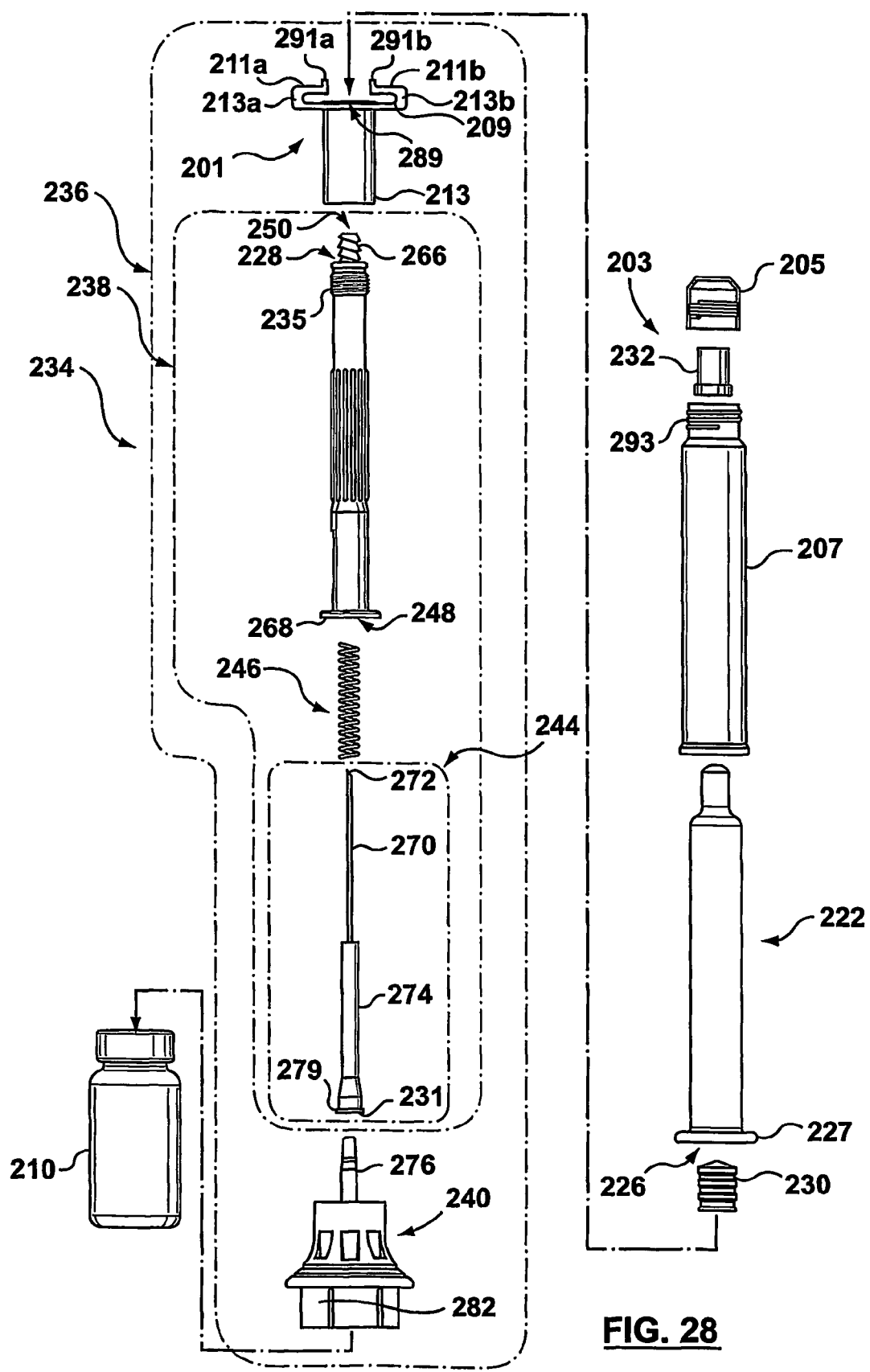
FIG. 28 is an exploded side elevational view of the pharmaceutical delivery system of FIG. 27.
Figure 29:
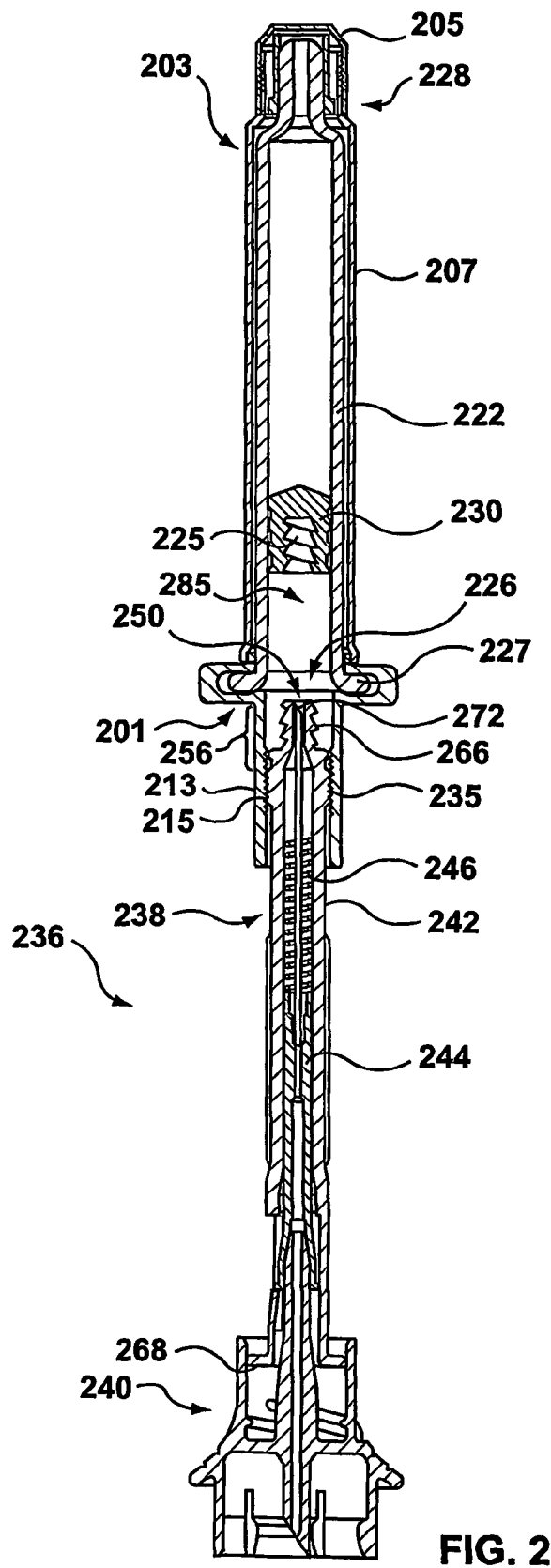
FIG. 29 is a cross-sectional view of the pharmaceutical transfer assembly of FIG. 27 attached to a syringe with a needle hub assembly in a retracted position relative to a housing and a transfer needle plunger rod in a first position relative to a backstop.

Referring now to FIGS. 29 and 32, the pharmaceutical transfer assembly of FIGS. 27-28 is shown generally at 236 with the needle transfer assembly 244 in a retracted position and the transfer needle plunger rod 238 in a first position. While in this configuration, the external thread 235 of the housing 242 is engaged with the internal thread 215 of the piston backstop 201. Additionally, the second portion 256 of the housing 242 is contained within the collar 213 of the piston backstop 201 and does not extend into the open end 226 of the syringe 222. This configuration has a number of advantages including that it permits sterilizing gas to pass through a gap 285 created between the second portion 256 of the housing 242 and the internal thread 235 of the piston 230, prevents accidental activation of the system since the needle transfer plunger rod 238 must be rotated to fully disengage the external thread 235 from the internal thread 215 of the piston stop 201 before the external thread 266 of needle transfer plunger rod can be threaded into the internal thread 225 of the piston 230, and permits the flange 227 of the syringe 222 to be inserted into the piston backstop 201 with ease since the flange 227 of the syringe 222 can be inserted into the piston backstop 201 without interference from the needle transfer plunger rod 238.

Figure 30:
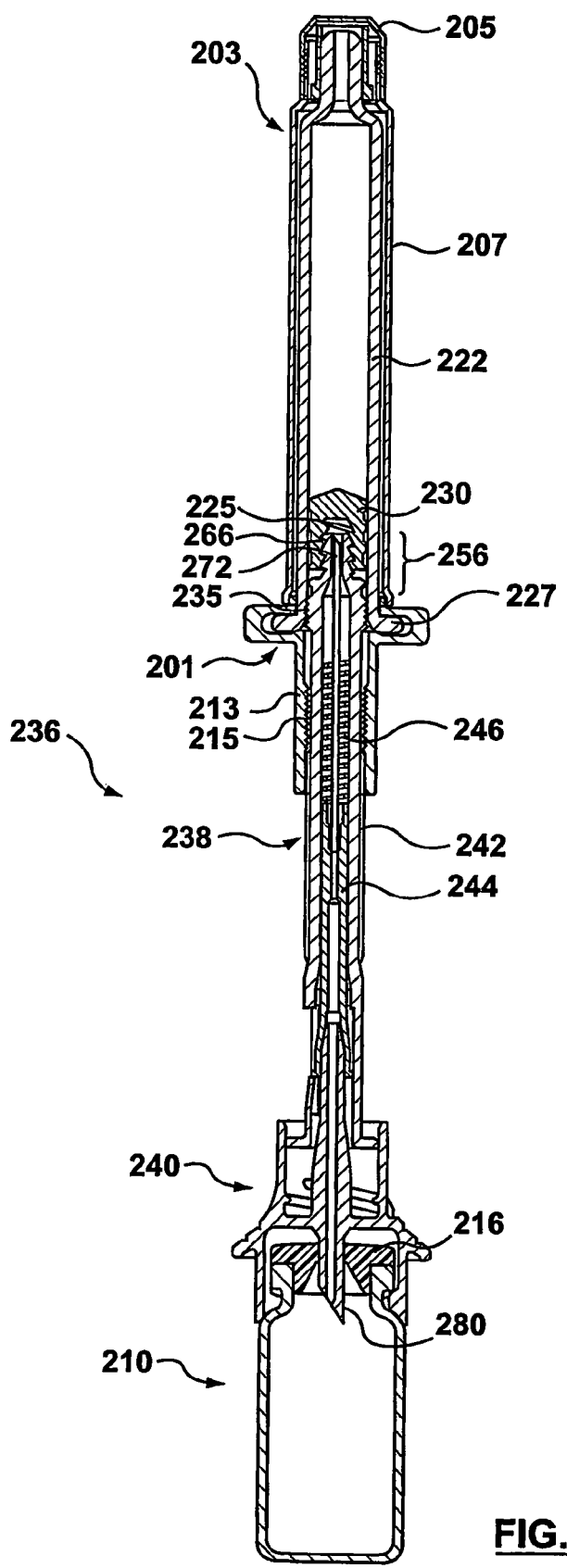
FIG. 30 is a cross-sectional view of the pharmaceutical transfer assembly of FIG. 27 attached to both a syringe and a vial with a needle hub assembly in a retracted position relative to a housing and a transfer needle plunger rod in a second position relative to a backstop.

FIG. 30 is a cross-sectional view of the pharmaceutical transfer assembly 236 with the needle hub assembly 244 in a retracted position and the needle transfer plunger rod 238 in a second position. While in this configuration, the external thread 235 of the housing 242 is fully disengaged from the internal thread 215 of the piston backstop 201. The second portion 256 of the housing 242 extends past the collar 213 of the piston stop 201 into the open end 226 of the syringe 222, and the external thread 266 of the housing 242 is engaged with the internal thread 225 in the piston 230. While in this configuration, the pharmaceutical transfer assembly is ready to be deployed. The piston 230 cannot be accidentally removed from the open end of the 226 of the syringe 222 by accidentally pulling on the vial, because a stop is created when the external thread 235 on the housing 242 abuts the internal thread 215 on the piston backstop 201.

Figure 31:
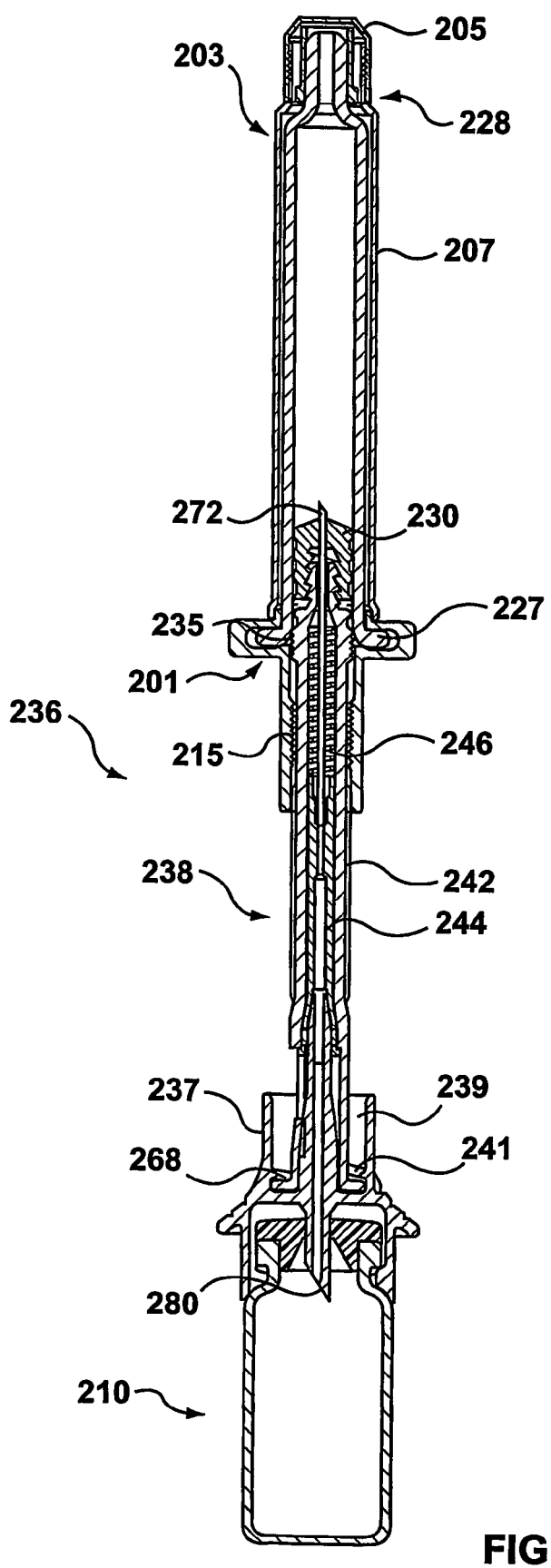
FIG. 31 is a cross-sectional view of the pharmaceutical transfer assembly of FIG. 27 attached to a syringe and a vial with a needle hub assembly in an advanced position relative to a housing and a transfer needle plunger rod in a second position relative to a backstop.
Figures 34, 35:
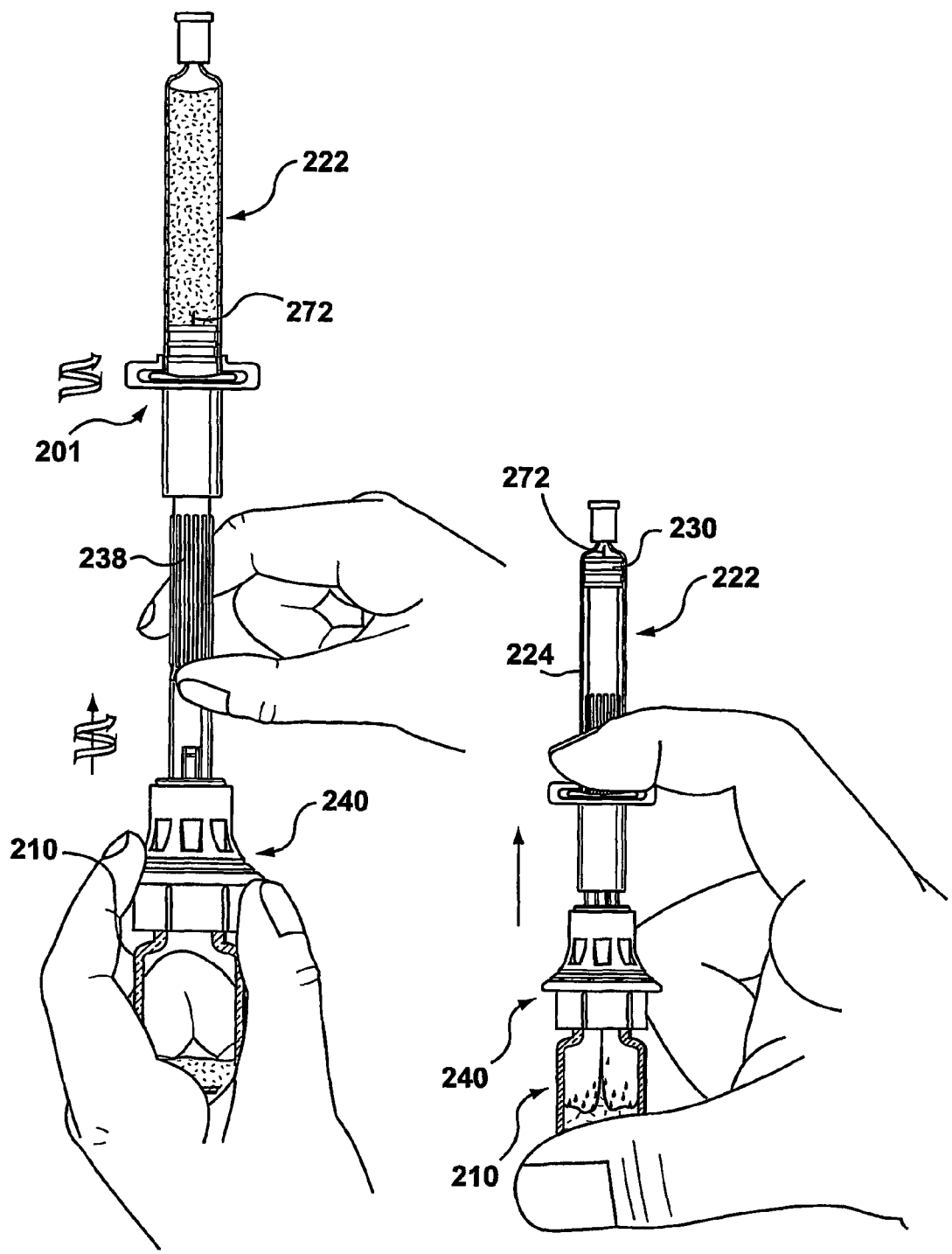

Referring now to FIGS. 31 and 34, the pharmaceutical transfer assembly 236 is shown with the needle hub assembly 244 in an advanced position and the needle transfer plunger rod 238 in a second position. The second portion 256 of the housing 242 extends past the collar 213 of the piston stop 201 into the open end 226 of the syringe 222, and the external thread 266 of the housing 242 is engaged with the internal thread 225 in the piston 230. While in this configuration, the flange 268 of the housing 242 is matingly engaged with the internal thread 241 positioned in the annular recess 239 of the collar 237. This creates fluid communication between the syringe 222 and the vial 210 when the vial 210 is inserted into the vial socket 240.

FIGS. 32-37 show the successive stages in the deployment of a pharmaceutical transfer assembly 236 shown in FIG. 27 to reconstitute a first fluid pharmaceutical component from a pre-filled syringe 222 with a second pharmaceutical component from a pharmaceutical vial 210. The second pharmaceutical component contained within the pharmaceutical vial 210 may be either a liquid or a solid (e.g. lyophilized powder).

Still referring to FIGS. 32-37, the method for deploying the pharmaceutical transfer assembly 236 is described in detail below. First, in step (a) the user threads the external thread 235 on the needle transfer plunger rod 238 into the internal thread 215 within the piston backstop 201. Then the user inserts to the post 276 of the vial socket assembly 240 into the needle hub 274 to create the assembly shown in FIGS. 29 and 32. Next, in step (b) the user removes the cover 220 of the pharmaceutical vial 210 (see FIG. 33). Then, in step (c) the user inserts and snap fits the pharmaceutical vial 210 into the vial socket 282 of the vial socket assembly 240 such that the tip 280 of the second hollow piercing member 278 penetrates the penetrable closure 216 on the pharmaceutical vial 210 (see FIG. 33). It is understood that step (a) can be performed first followed by steps (b) and (c) in that order, or steps (b) and (c) can be performed first in that order followed by step (a).

After completing steps (a), (b), and (c), in step (d) the user threads the needle transfer plunger rod 238 so that the external thread 235 on the housing 242 becomes fully disengaged from the internal thread 215 on the piston backstop 201 and the external thread 266 matingly engages the internal thread 225 on the piston 230 (see FIG. 30). Next, in step (e) the user advances both the pharmaceutical vial 210 and the vial socket assembly 240 forward towards the syringe 222 and locks the vial socket assembly 240 to the housing 242 by threading the flange 268 of the housing 242 into the internal thread 241 formed in the annular recess 239 of the collar 237 of the vial socket 240. This, in turn, advances the tip 272 of the first hollow piercing member longitudinally within the bore 252 of the housing 242 from the retracted position to the advanced position wherein the tip 272 of the first hollow piercing member 270 penetrates completely through the piston 230 into the body of the syringe 222. With both tip 272 and tip 280 having pierced their respective items, this creates fluid communication between the pharmaceutical vial 210 and the syringe 222 (see FIGS. 31 and 34).

Next in step (f) the user advances the vial 210 longitudinally towards the syringe 222. This moves the piston 230 within the syringe 222 forcing the fluid within the syringe body 224 into and through the needle assembly 244 and through the vial socket assembly 240 to inject the first fluid pharmaceutical component into the pharmaceutical vial 210 (see FIG. 35). Then, in step (g) the user swirls the pharmaceutical delivery system 234 to dissolve, dilute or suspend the first fluid pharmaceutical component into the second pharmaceutical component.

Next in step (h), the user inverts the pharmaceutical delivery system 234 and withdraws the vial 210 longitudinally away from the syringe 222 to aspirate the now mixed contents of the pharmaceutical vial 210 into the syringe 222 (see FIG. 36). The piston 230 cannot be accidentally removed from the open end of the 226 of the syringe 222 during this step by merely withdrawing the vial away from the syringe, because a stop is created when the external thread 235 on the housing 242 abuts the internal thread 215 on the piston backstop 201.

In step (i), the user detaches the vial socket assembly 240 from the needle transfer plunger rod 238 (by unthreading the two and pulling the post 276 of the vial socket assembly 240 out of the needle hub 274) to provide a filled syringe 222 ready for use (see FIG. 37). To use the filled syringe, the user removes the tip cap 232 and attaches a needle (not shown). The needle transfer plunger rod 238 forms the plunger to discharge the mixed pharmaceutical from the syringe 222 through the attached needle.

It will be understood by a person skilled in the art that once the user detaches the vial socket assembly 240 from the needle transfer plunger rod 238 (by unthreading the two), the resilient biasing member 246 retracts the first hollow piercing member back to the retracted or "inactivated" position. As such, the piston 230 reseals to prevent fluid communication between the syringe 222 and the needle transfer plunger rod 238. Accordingly, when the user uses syringe 222 to deliver the reconstituted multi-component pharmaceutical to a patient or IV line, the user simply depresses the needle transfer plunger rod 238 in a conventional manner.

Figure 42:
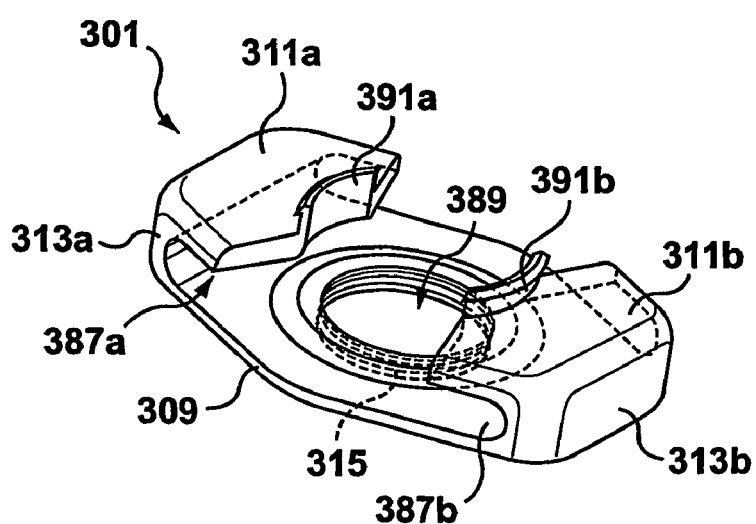
FIG. 42 is a perspective view of a backstop according to a further aspect of the present invention.

FIG. 42 shows another embodiment of a piston backstop 301 according to the present invention. The piston backstop 301 has a bottom plate 309 with an aperture 389, two top plate extensions 311*a*, 311*b*, and two side walls 313*a*, 313*b* connecting the bottom plate 309 to the two top plate extensions 311*a*, 311*b*. In this arrangement, the bottom plate 309, sidewalls 313*a*, 313*b*, and the top plate extensions 311*a*, 311*b* form a pair of gaps 387*a*, 387*b* that is sized to snugly receive the flange 227 of the syringe 222. An inner surface defining the aperture 389 has a retaining member (which in the illustrated embodiment is an internal thread 315), and an inner diameter that is slightly larger than the outer diameter of the detachable needle transfer plunger rod 238 to permit the needle transfer plunger rod to move axially within the piston stop 301. The piston backstop 301 may have a pair of snaps 391*a*, 391*b* positioned on the two top plate extensions 311*a*, 311*b* to permit attachment of the sheath 207. The primary difference between the piston backstop shown in FIG. 42 and the one previously described in FIG. 41 is that the internal thread 315 is located in the inner surface defining the aperture 389, whereas in the previously described embodiment the internal thread 215 is located in the collar 213.

FIGS. 38-40 show the piston backstop 201 being used with a pre-filled syringe 222 having a slightly modified plunger rod 238*a* according to a further aspect of the present invention. Plunger rod 238*a* is a conventional plunger rod having an external thread 235 that is shaped and sized to matingly cooperate with the internal thread 215 of the piston backstop 201. In a similar manner, the piston backstop 201 can be connected to a flange 227 of the pre-filled syringe 222 to facilitate sterilization of the pre-filled syringe 222, to prevent accidental activation of the pre-filled syringe 222, and to prevent a piston 230 from being accidentally dislodged from the open end 226 of the syringe 222.

FIG. 39 shows a pre-filled syringe 222 ready to be sterilized. While in this configuration, the external thread 235 of the plunger rod 238*a* is engaged with the internal thread 215 of the piston backstop 201. Additionally, the plunger rod 238*a* is contained within the collar 213 of the piston backstop 201 and does not extend into the open end 226 of the syringe 222. This configuration has a number of advantages including that it permits sterilizing gas to pass through a gap 285 created between the plunger rod 238*a* and the internal thread 235 of the piston 230, prevents accidental activation of the prefilled syringe 222, and permits the flange 227 of the syringe 222 to be inserted into the piston backstop 201 with ease since the flange 227 of the syringe 222 can be inserted into the piston backstop 201 without interference from the plunger rod 238*a*.

FIG. 40 shows a pre-filled syringe ready to be deployed. While in this configuration, the external thread 235 of the plunger rod 238*a* is disengaged from the internal thread 215 of the piston backstop 201. The plunger rod 238*a* extends past the collar 213 of the piston stop 201 into the open end 226 of the syringe 222, and the external thread 266 of the housing 242 is engaged with the internal thread 225 in the piston 230. The piston 230 cannot be accidentally removed from the open end of the 226 of the syringe 222 by accidentally pulling on the plunger rod 238*a*, because a stop is created when the external thread 235 on the plunger rod 238*a* abuts the internal thread 215 on the piston backstop 201.

Figure 43:
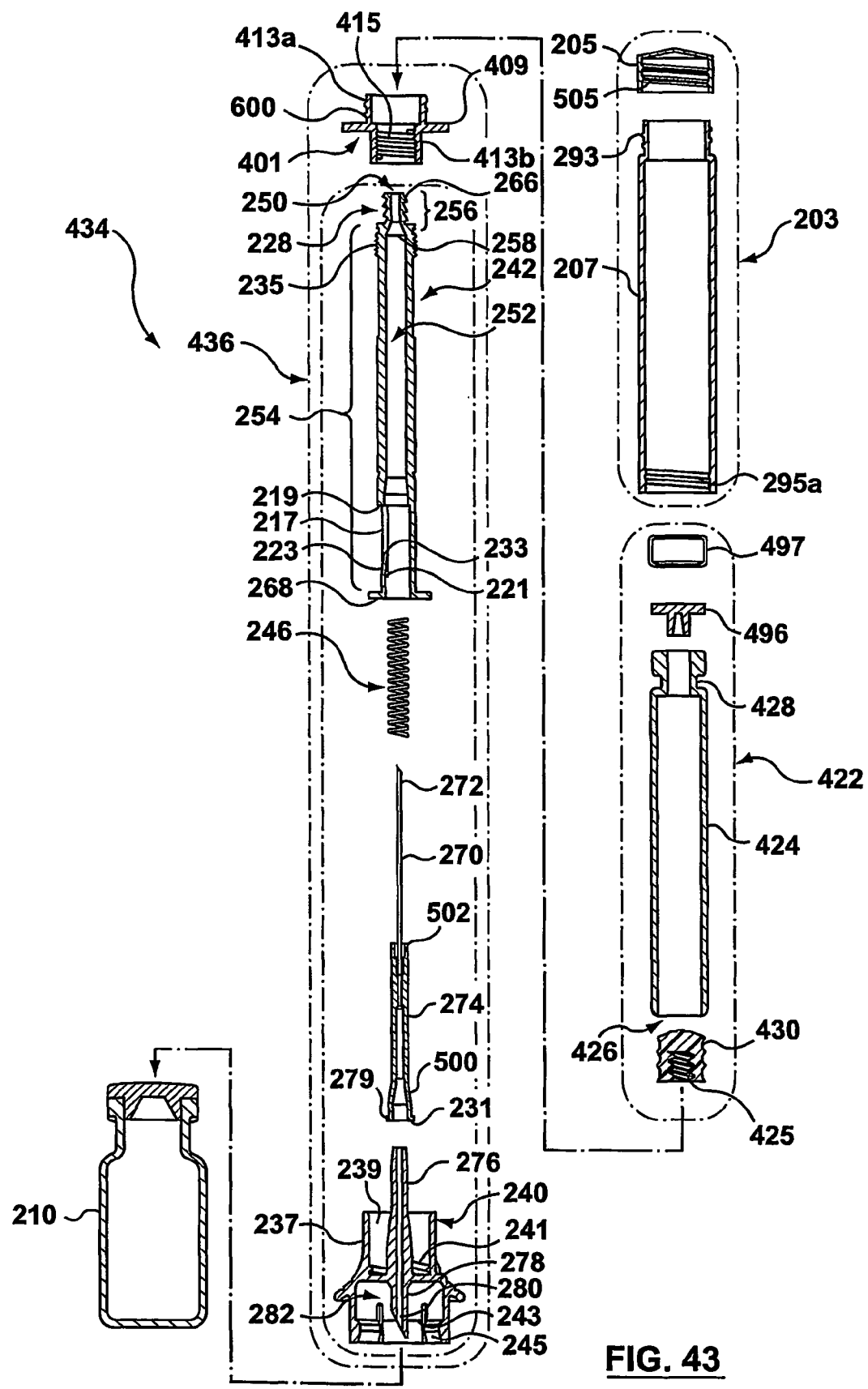
FIG. 43 is an exploded cross-sectional view of a pharmaceutical delivery system including a pharmaceutical transfer assembly according to a further aspect of the present invention.
Figures 44, 45:
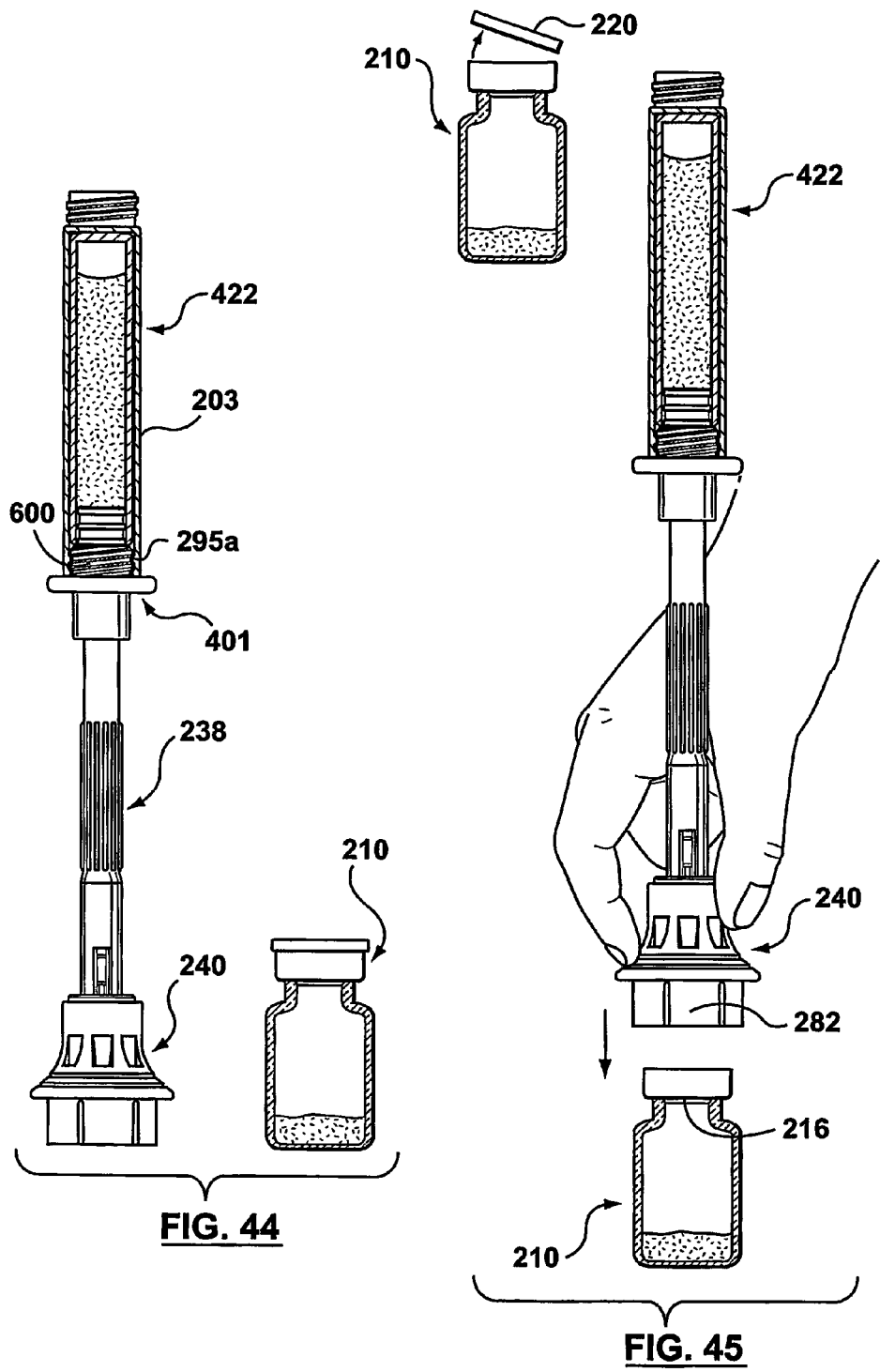

Referring now to FIG. 43, a pharmaceutical delivery system made in accordance with another aspect of the present invention is shown generally at 434. The pharmaceutical delivery system 434 shown in FIGS. 43-51 is the same as the pharmaceutical delivery system 234 of FIGS. 27-37, except as described in detail below. In particular, the pharmaceutical delivery system 434 shown in FIG. 43 includes a cartridge 422 (instead of a syringe), a modified sheath assembly 203, and a modified piston backstop 401 that cooperates with the modified sheath assembly 203 to facilitate the deployment of the system 434.

Cartridge 422 has a body 424 being open at one end 426 and having a neck 428 at the opposite end. A piston 430 is lodged in the body 424 proximate the open end 426. The piston 430 has an internal thread 425 that matingly threads with the thread on the detachable needle transfer plunger rod 238. The neck 428 of the cartridge 422 has a reduced diameter compared with the body 424. A penetrable closure 496 has a body 496a and a flange 496b, and is preferably made of an elastomeric material (e.g. rubber). The body 496a is sized to fit snugly within the neck 428. A cap 497 holds the penetrable closure 496 in the neck 428 of the cartridge 422.

The sheath assembly 203 generally has a plastic cap 205 having an internal thread 505, and a hard body sheath 207 having a corresponding external thread 293 and an internal thread 295a. The sheath assembly 203 helps protect the cartridge 422 from breakage during both transport and deployment of the pharmaceutical transfer system 434. Additionally, the sheath assembly 203 facilitates the assembly and deployment of the pharmaceutical delivery system 434, as will be subsequently described in more detail below.

The piston backstop 401 may be connected to the sheath assembly 203 to facilitate sterilization of the transfer assembly 436, to prevent accidental activation of the pharmaceutical delivery system 434, and to prevent the piston 430 from being accidentally dislodged from the open end 426 of the cartridge 422. The piston backstop 401 has a preferably cylindrical collar 413 having an upper portion 413a and a lower portion 413b, and a flange 409 extending radially from the intersection between the upper and lower portions 413a, 413b of the collar. The collar 413a, 413b has an internal diameter that is slightly larger than the outer diameter of the detachable needle transfer plunger rod 238 to permit the needle transfer plunger rod 238 to move axially within the piston stop 401. The upper portion of the collar 413a has an external thread 600 that matingly cooperates with the internal thread 295a of the sheath assembly 203 to permit the two components to be threaded together. The lower portion of the collar 413b has an internal thread 415 that matingly cooperates with an external thread 235 of the needle transfer plunger rod 238 to permit the two components to be threaded together.

FIGS. 44-51 show the successive stages in the deployment of the pharmaceutical transfer assembly 436 shown in FIG. 43 to reconstitute a first fluid pharmaceutical component from a pre-filled cartridge 422 with a second pharmaceutical component from a pharmaceutical vial 210. The second pharmaceutical component contained within the pharmaceutical vial 210 may be either a liquid or a solid (e.g. lyophilized powder).

Still referring to FIGS. 44-51, the method for deploying the pharmaceutical transfer assembly 436 is described in detail below. First, in step (a) the user threads the external thread 600 on the piston backstop 401 into the internal thread 295a on the sheath assembly 203. Then the user threads external thread 235 on the needle transfer plunger rod 238 into the internal thread 415 within the piston backstop 401. Then the user inserts the post 276 of the vial socket assembly 240 into the needle hub 274 to create the assembly shown in FIG. 44. Next, in step (b) the user removes the cover 220 of the pharmaceutical vial 210 (see FIG. 45). Then, in step (c) the user inserts and snap fits the pharmaceutical vial 210 into the vial socket 282 of the vial socket assembly 240 such that the tip 280 of the second hollow piercing member 278 penetrates the penetrable closure 216 on the pharmaceutical vial 210 (see FIG. 45). It is understood that step (a) can be performed first followed by steps (b) and (c) in that order, or steps (b) and (c) can be performed first in that order followed by step (a).

After completing steps (a), (b), and (c), in step (d) the user advances the needle transfer plunger rod 238 by rotation until the external thread 235 on the housing 242 fully disengages from the internal thread 415 on the piston backstop 401 and external thread 266 matingly engages the internal thread 425 on the piston 430. Next, in step (e) the user advances both the pharmaceutical vial 210 and the vial socket assembly 240 forward toward the cartridge 422, and threads the flange 268 of the housing 242 into the internal thread 241 formed in the annular recess 239 of the collar 237 of the vial socket 240 to lock the vial socket assembly 240 onto the housing 242. This, in turn, advances the tip 272 of the first hollow piercing member longitudinally within the bore 252 of the housing 242 from the retracted position to the advanced position wherein the tip 272 of the first hollow piercing member 270 penetrates completely through the piston 430 into the body 424 of the cartridge 422. This creates fluid communication between the pharmaceutical vial 210 and the cartridge 422 (see FIG. 46).

Next in step (f) the user advances the vial 210 longitudinally towards the cartridge 422. This moves the piston 430 within the cartridge 422 forcing the fluid within the cartridge body 424 into and through the needle assembly 244, through the vial socket assembly 240, and into the pharmaceutical vial 210 (see FIG. 47). Then, in step (g) the user swirls the pharmaceutical delivery system 434 to dissolve, dilute or suspend the first fluid pharmaceutical component into the second pharmaceutical component.

Figures 46, 47, 48:
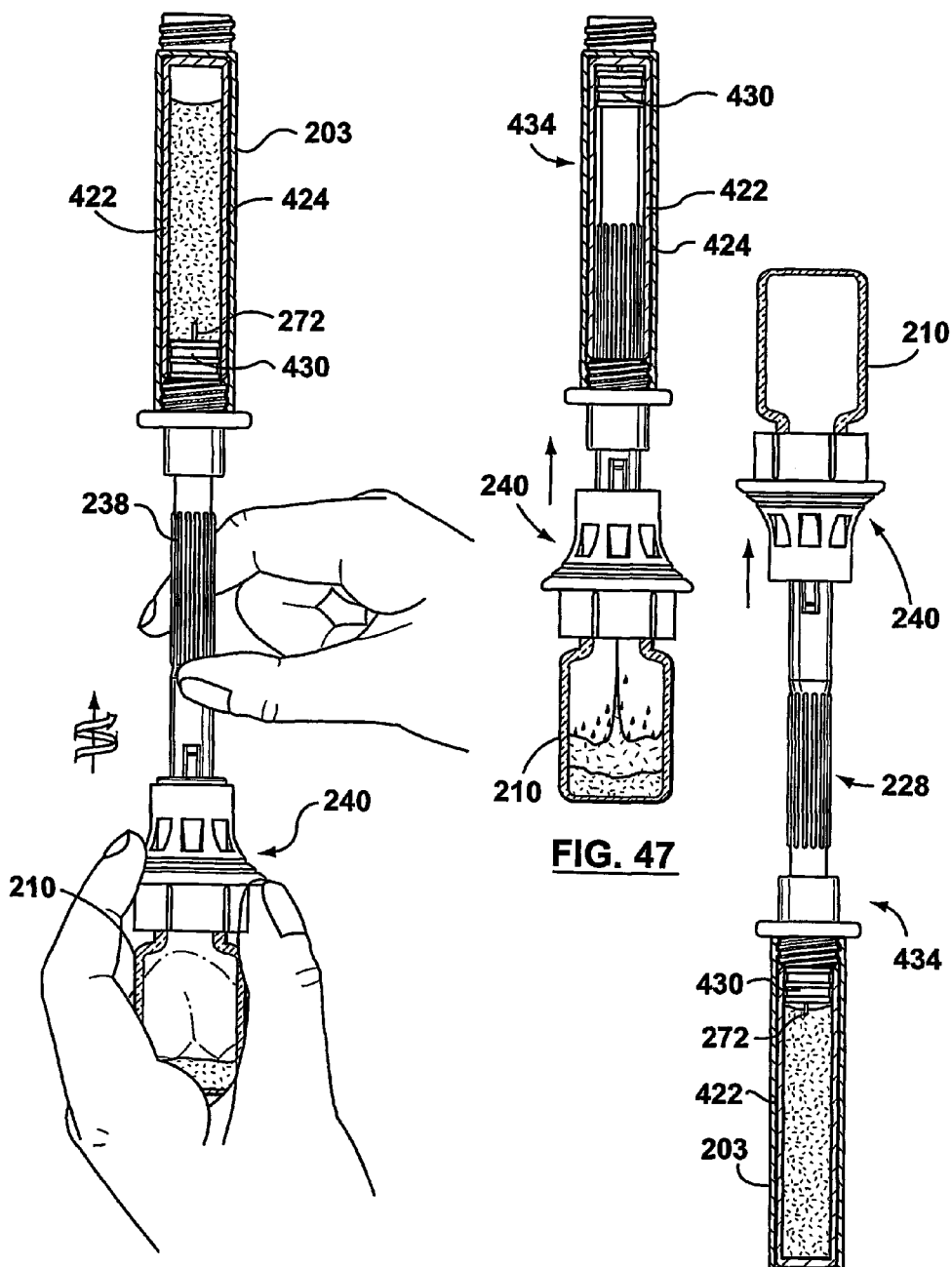

Next in step (h), the user inverts the pharmaceutical delivery system 434 and withdraws the vial 210 longitudinally away from the cartridge 422 to aspirate the now mixed contents of the pharmaceutical vial 210 into the cartridge 422 (see FIG. 48). The piston 430 cannot be accidentally removed from the open end of the 426 of the cartridge 422 during this step by merely withdrawing the vial 210 away from the cartridge 422, because a stop is created when the external thread 235 on the housing 242 abuts the internal thread 415 on the piston backstop 401.

In step (i), the user unlocks the vial socket assembly 240 from the housing 242 by unthreading the two (see FIG. 49). In step (j), the user removes the sheath assembly 203 from the piston backstop 401 by unthreading the two (see FIG. 50). In step (k), the user detaches the cartridge 422 from the transfer assembly 436 by unthreading the two (see FIG. 51). The cartridge 422 containing the reconstituted multi-component pharmaceutical may now be used in any conventional application, such as, for example, a pen injector or an auto injector.

Figure 52:
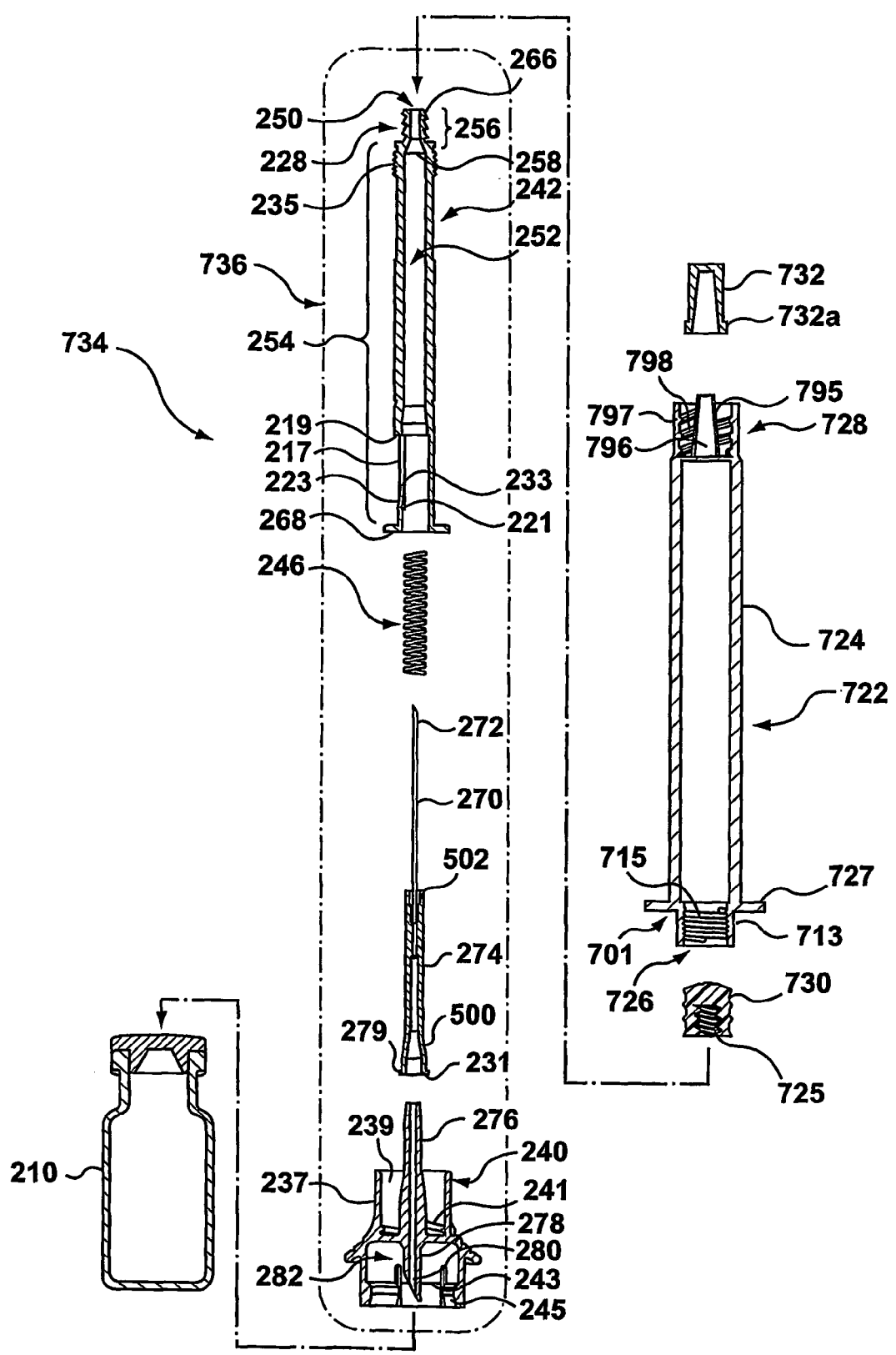
FIG. 52 is an exploded cross-sectional view of a pharmaceutical delivery system including a pharmaceutical transfer assembly according to a further aspect of the present invention.

Referring now to FIG. 52, a pharmaceutical delivery system made in accordance with another aspect of the present invention is shown generally at 734. The pharmaceutical delivery system 734 shown in FIG. 52 is the same as the pharmaceutical delivery system 234 of FIGS. 27-37, except as described in detail below. In particular, the pharmaceutical delivery system 734 shown in FIG. 52 includes a modified plastic molded syringe 722 having an integrally molded modified piston backstop 701 proximate an open end 726 of a syringe body 724.

Plastic syringe 722 has a body 724 being open at one end 726 and having a neck 728 at its opposite end. A piston 730 is lodged snugly in the syringe body 724 from the open end 726, the piston 730 being provided with an internal thread 725 that matingly threads with the thread on the detachable needle transfer plunger rod 238 A flange 727 is provided adjacent the open end 726 of the syringe body 724. The neck 728 of the syringe body 724 has a needle mount (which in the illustrated embodiment is a standard needle coupling or "luer lock" comprising a conical spigot 795 with a central passage 796 communicating with the syringe body 724, surrounded by a cylindrical sleeve 797 having an internal thread 798). The neck 728 of the syringe body 724 is sealed with a tip cap 732 having an external flange 732a. The syringe 722 has an integrally molded modified piston backstop 701 at the open end 726 of the syringe body 724.

The integrally molded piston backstop 701 can be used to facilitate sterilization of the transfer assembly 736, to prevent accidental activation of the pharmaceutical delivery system 734, and to prevent a piston 730 from being accidentally dislodged from the open end 726 of the syringe 722. The integrally molded piston backstop 701 has a preferably cylindrical collar 713. Collar 713 has an internal thread 715, and an inner diameter that is slightly larger than the outer diameter of the detachable needle transfer plunger rod 238 to permit the needle transfer plunger rod 238 to move axially within the piston stop 701.

It will be appreciated by one skilled in the art that the method of deploying the pharmaceutical transfer assembly 734 in FIG. 52 is the same as the method of deploying the pharmaceutical transfer assembly 234 in FIG. 27.

Figure 53:
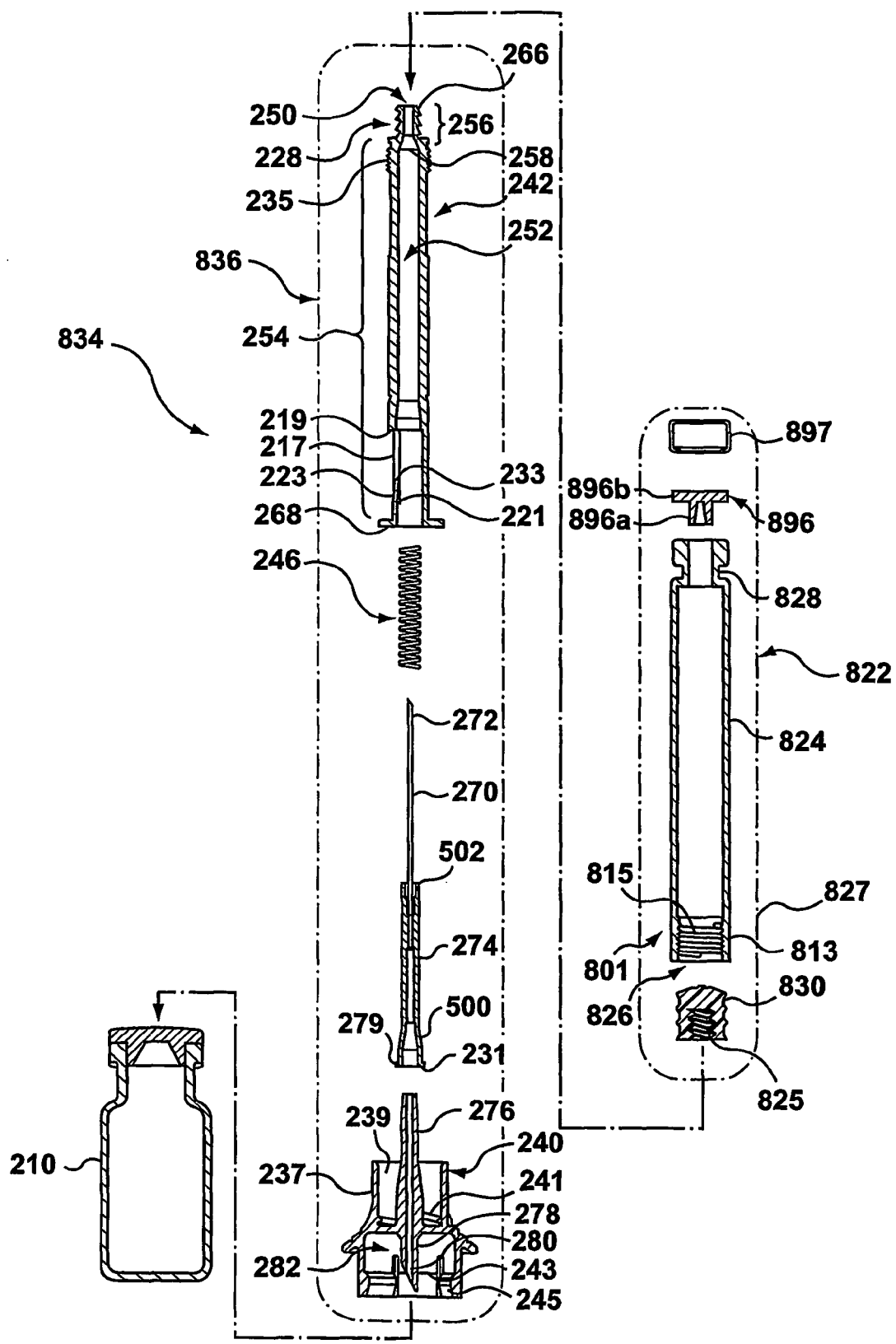
FIG. 53 is an exploded cross-sectional view of a pharmaceutical delivery system including a pharmaceutical transfer assembly according to a further aspect of the present invention.

Referring now to FIG. 53, a pharmaceutical delivery system made in accordance with another aspect of the present invention is shown generally at 834. The pharmaceutical delivery system 834 shown in FIG. 53 is the same as the pharmaceutical delivery system 734 of FIG. 52, except as described in detail below. In particular, the pharmaceutical delivery system 834 shown in FIG. 53 includes a modified plastic molded cartridge 822 having an integrally molded modified piston backstop 801 at an open end 826 of a cartridge body 824.

Plastic cartridge 822 has a body 824 being open at one end 826 and having a neck 828 at the opposite end. A piston 830 is lodged in the body 424 proximate the open end 426. The piston 830 has an internal thread 825 that matingly threads with the thread on the detachable needle transfer plunger rod 238. The neck 828 of the cartridge 822 has a reduced diameter compared with the body 824. A penetrable closure 896 has a body 896a and a flange 896b, and is preferably made of an elastomeric material (e.g. rubber). The body 896a is sized to fit snugly within the neck 828. A cap 897 holds the penetrable closure 896 in the neck 828 of the cartridge 822.

The integrally molded piston backstop 801 can be used to facilitate sterilization of the transfer assembly 836, to prevent accidental activation of the pharmaceutical delivery system 834, and to prevent a piston 830 from being accidentally dislodged from the open end 726 of the cartridge 822. The integrally molded piston backstop 801 has a preferably cylindrical collar 813 with an internal thread 815, and an inner diameter that is slightly larger than the outer diameter of the detachable needle transfer plunger rod 238 to permit the needle transfer plunger rod 238 to move axially within the piston stop 801.

It will be appreciated by one skilled in the art that the method of deploying the pharmaceutical transfer assembly 836 in FIG. 53 is the same as the method of deploying the pharmaceutical transfer assembly 234 in FIG. 27.

While the above description constitutes the preferred embodiments, it will be appreciated that the present invention is susceptible to modification and change without departing from the fair meaning of the proper scope of the accompanying claims.

The invention claimed is:

1. An assembly for transferring a fluid from a vessel having a body with a reduced diameter neck at one end thereof and other end being open, a slidable piston positioned within the body through the open end, and a vial having a penetrable seal, the assembly comprising:
a) a housing having first and second open ends and a bore extending between the first and second open ends, the housing being removably connectable to the piston through said open end of said vessel;
b) a conduit having first and second ends and first and second apertures adjacent to the first and second ends, respectively, the conduit being longitudinally slidable within the bore between a retracted position in which the first aperture is positioned within the housing and an activated position in which the first aperture protrudes through the piston into the body of the vessel when the housing is connected to the piston, said bore having a first portion thereof sized such that said housing provides support to said conduit;
c) a biasing member mounted within a second portion of said bore and being configured to exert pressure on said conduit when said conduit is in the activated position;
d) a vial socket assembly having a vial socket for receiving and engaging a neck portion of the vial and a hollow piercing member having a first open end in fluid communication with the conduit and a second open end for piercing the penetrable seal, the vial socket assembly moveable longitudinally relative to the housing in concert with the conduit, a second end of said conduit being releasably connected to said vial socket assembly;
whereby advancing the vial socket assembly longitudinally towards the housing advances the conduit from the retracted position to the activated position to fluidly connect the vessel and the vial.

2. An assembly according to claim 1 wherein the first end of the conduit has a piercing member and the aperture is an opening adjacent to a tip of the piercing member.

3. An assembly according to claim 2 wherein said second end of said conduit has a hub for connecting to said vial socket assembly.

4. An assembly according to claim 3 wherein the vial socket assembly further comprises a post for receiving said second end of said conduit.

5. An assembly according to claim 4 wherein the hub forms a female luer slip and the post forms a male luer slip that is releasably receivable in the female luer slip.

6. An assembly according to claim 5 wherein the bore of the housing has a first portion, a second portion adjacent to the first portion, and a shoulder formed between the first and second portions.

7. An assembly according to claim 6 wherein said resilient biasing member is positioned between the shoulder and the hub to bias the conduit into the retracted position.

8. An assembly according to claim 7 wherein the resilient biasing member is a spring.

9. An assembly according to claim 1 wherein the first end of the conduit has a blunt end and the first aperture is an opening on a sidewall of the conduit.

10. An assembly according to claim 1 further comprising a retaining member in the vial socket for retaining a vial within the vial socket.

11. An assembly according to claim 10, wherein the retaining member comprises an annular ridge on an interior surface of the vial socket, the annular ridge having a smaller diameter than the diameter of the vial socket.

12. An assembly according to claim 10, wherein the retaining member comprises a plurality of retaining latches provided in the vial socket.

13. An assembly according to claim 1 wherein the vessel is a syringe having a neck with a needle mount for removably mounting a needle thereon and a flange adjacent the open end.

14. An assembly according to claim 13 further comprising a piston backstop positioned adjacent the flange, the piston backstop having a retaining member for retaining the housing in spaced relation from the piston.

15. An assembly according to claim 14 wherein the piston backstop is shaped and sized to slidably receive the housing.

16. An assembly according to claim 15 wherein the piston backstop is removably connectable to the flange.

17. An assembly according to claim 16 wherein the syringe is glass.

18. An assembly according to claim 17 further comprising a sheath assembly positioned over the neck of the syringe, the sheath assembly removably connectable to the piston backstop.

19. An assembly according to claim 14 wherein the syringe is plastic and the piston backstop is integrally molded with the syringe.

20. An assembly according to claim 1 wherein the vessel is a cartridge having a neck with a penetrable closure and a cap to retain the penetrable closure thereon.

21. An assembly according to claim 20 further comprising a sheath assembly positioned over the neck of the cartridge and a piston backstop removably connectable to the sheath assembly, the piston backstop having a retaining member for retaining the housing in spaced relation from the piston.

22. An assembly according to claim 20 further comprising a piston backstop positioned adjacent the open end of the cartridge, the piston backstop having a retaining member for retaining the housing in spaced relation from the piston.

23. An assembly according to claim 22 wherein the cartridge is plastic and the piston backstop is integrally molded with the cartridge.

24. In combination, a syringe having a syringe body, a fluid within said syringe body, a first end of said syringe body being open, a slidable piston positioned within the body proximate the open end, a second end having a neck with a needle mount for removably mounting a needle thereon;

a vial having a penetrable seal, said vial containing a medicant;

a transfer assembly for transferring a fluid from said syringe to said vial and subsequently retransferring the medicant and fluid to said syringe, the assembly comprising a housing having first and second open ends and a bore extending between said first and second open ends, the housing being removably connected to the piston;

a conduit having first and second ends and first and second apertures adjacent to said first and second ends respectively, the conduit being longitudinally slidable within the bore between a retracted position wherein the first aperture is positioned within the housing and an activated position in which said first aperture projects through the piston into the body of the vessel said bore having a portion thereof sized such that said housing provides support to said conduit;

a biasing member mounted within a second portion of said bore and being configured to exert pressure on said conduit when said conduit is in the activated position;

a vial socket assembly having a vial socket for receiving and engaging at least a portion of the vial including the penetrable seal, a hollow piercing member having a first open end in fluid communication with the conduit and a second open end having a spike for piercing the penetrable seal, the vial socket assembly being moveable longitudinally relative to the housing in concert with said conduit, a second end of said conduit being releasably connected to said vial socket assembly;

the arrangement being such that advancing the vial socket assembly longitudinally towards the housing advances the conduit from the retracted position to an activated position to fluidly connect the vessel and the vial.

25. The combination according to claim 24 wherein the first end of the conduit has a piercing member and the first aperture is an opening adjacent to a tip of the piercing member.

26. The combination according to claim 25 wherein said second end of said conduit has a hub connected to said vial socket assembly.

27. The combination according to claim 26 wherein the vial socket assembly further comprises a post on which said second end of said conduit is mounted.

28. The combination according to claim 27 wherein the hub forms a female luer slip and the post forms a male luer slip that is releasably received in the female luer slip.

29. The combination according to claim 28 wherein the bore of the housing has a first portion, a second portion adjacent to the first portion, and a shoulder formed between the first and second portions.

30. The combination according to claim 29 wherein said resilient biasing member is positioned between the shoulder and the hub to bias the conduit into the retracted position.

31. The combination according to claim 30 wherein the resilient biasing member is a spring.

32. The combination according to claim 24, including a retaining member for said vial and which comprises an annular ridge on an interior surface of the vial socket, the annular ridge having a smaller diameter than the diameter of the vial socket.

33. The combination according to claim 32, wherein the retaining member comprises a plurality of retaining latches provided in the vial socket.

34. The combination according to claim 24 wherein the vessel is a syringe having a neck with a needle mount for removably mounting a needle thereon and a flange adjacent the open end.

35. The combination according to claim 34 further comprising a piston backstop positioned adjacent the flange, the piston backstop having a retaining member for retaining the housing in spaced relation from the piston.

36. The combination according to claim 35 wherein the piston backstop is shaped and sized to slidably receive the housing.

37. The combination according to claim 36 wherein the piston backstop is removably connectable to the flange.

38. The combination according to claim 35 further comprising a sheath assembly positioned over the neck of the syringe, the sheath assembly removably connectable to the piston backstop.

39. The combination according to claim 35 wherein the syringe is plastic and the piston backstop is integrally molded with the syringe.

40. The combination according to claim 24 further comprising a sheath assembly positioned over the neck of the cartridge and a piston backstop removably connectable to the sheath assembly, the piston backstop having a retaining member for retaining the housing in spaced relation from the piston.

\* \* \* \* \*